US009918964B2

(12) United States Patent
Collman et al.

(10) Patent No.: US 9,918,964 B2
(45) Date of Patent: Mar. 20, 2018

(54) REDUCING PLATELET ACTIVATION, AGGREGATION AND PLATELET-STIMULATED THROMBOSIS OR BLOOD COAGULATION BY REDUCING MITOCHONDRIAL RESPIRATION

(75) Inventors: James P. Collman, Stanford, CA (US); Paul Clifford Herrmann, Loma Linda, CA (US); David Alvin Tyvoll, La Jolla, CA (US); Richard Decreau, Cedex (FR); Brian Stanley Bull, Loma Linda, CA (US); Christopher Jeffrey Barile, San Carlos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 788 days.

(21) Appl. No.: 13/093,825

(22) Filed: Apr. 25, 2011

(65) Prior Publication Data

US 2011/0301180 A1     Dec. 8, 2011

Related U.S. Application Data

(60) Provisional application No. 61/327,613, filed on Apr. 23, 2010.

(51) Int. Cl.

| | |
|---|---|
| *A61K 31/41* | (2006.01) |
| *A61K 31/385* | (2006.01) |
| *A61K 31/404* | (2006.01) |
| *A61K 31/4164* | (2006.01) |
| *A61K 31/4192* | (2006.01) |
| *A61K 31/426* | (2006.01) |
| *A61K 31/505* | (2006.01) |
| *C07F 9/6539* | (2006.01) |

(52) U.S. Cl.
CPC .......... *A61K 31/385* (2013.01); *A61K 31/404* (2013.01); *A61K 31/41* (2013.01); *A61K 31/4164* (2013.01); *A61K 31/4192* (2013.01); *A61K 31/426* (2013.01); *A61K 31/505* (2013.01); *C07F 9/6539* (2013.01)

(58) Field of Classification Search
CPC ............................ A61K 31/41; A61K 31/4192
USPC ................. 514/183, 381, 439, 822, 824
See application file for complete search history.

(56) References Cited

U.S. PATENT DOCUMENTS

| 7,078,423 B2 * | 7/2006 | Nivorozhkin | ........ C07D 257/04 |
| | | | 514/381 |
| 7,312,214 B2 * | 12/2007 | Qiao et al. | ................. 514/230.5 |

FOREIGN PATENT DOCUMENTS

| CN | 101786993 A | 7/2010 |
| WO | WO2003064400 A1 | 8/2003 |

OTHER PUBLICATIONS

Katritzky et al., Journal of Organic chemistry, 2003, 4941-4943.*
Poredos et al., Int Angiol.Dec. 2007; 26(4):306-11.*
Roth et al., Blood, vol. 83, No. 4, 1994: pp. 885-898 Wu et al., Circulation, 1976, No. 53, 687-691.*
Lekstrom et al. Medicine, vol. 70, 1991, pp. 161-178 Pappas et al., Arch Pathol Lab Med. 1994, 118:801-804.*
Simon et al., J Allergy Clinical Immunology, 2003, 109-118.*
Gawaz et al., The Journal of Clinical Investigation, vol. 115, No. 12, Dec. 2005, pp. 3378-3384.*
Ute et al. Journal of Medicinal Chemistry, Jan. (2010), 53(3), 1172-1189,.*
Borsig, Expert Review of Anticancer Therapy, 1247-1255, 2008.*
Alterman et al., "Fast Microwave-Assisted Preparation of Aryl and Vinyl Nitriles and the Corresponding Tetrazoles from Organohalides", 2000, pp. 7984-7989, vol. 65, Publisher: J. Org. Chem.
Amantini et al., "Synthesis of 4-Aryl-1H-1,2,3-triazoles through TBAF-Catalyzed [3 + 2] Cycloaddition of 2-Aryl-1-nitroethenes with TMSN3 under Solvent-Free Conditions", "J. Org. Chem.", 2005, pp. 6526-6529, vol. 70.
Andersen et al., "Efficient One-Pot Synthesis of 1-Aryl 1,2,3-Triazoles from Aryl Halides and Terminal Alkynes in the Presence of Sodium Azide", "Synlett.", 2005, pp. 2941-2947, vol. 19.
Brown et al., "Targeting lipoic acid to mitochondria: Synthesis and characterization of a triphenylphosphonium-conjugated a-lipoyl derivative", "Free Radical Bio. Med.", 2007, pp. 1766-1780, vol. 42.
Butler et al., "A Ceric Ammonium Nitrate N-Dearylation of N-p-Anisylazoles Applied to Pyrazole, Triazole, Tetrazole, and Pentazole Rings: Release of Parent Azoles. Generation of Unstable Pentazole,HN5/N5-, in Solution", 2007, "J. Org. Chem." pp. 1354-1364, vol. 73.
Das et al., "A Simple, Advantageous Synthesis of 5-Substituted 1H-Tetrazoles", "Synlett.", 2010, pp. 391-394, vol. 3.
Demko et al., "A Click Chemistry Approach to Tetrazoles by Huisgen 1,3-Dipolar Cycloaddition: Synthesis of 5-Acyltetrazoles from Azides", "Angew. Chem. Int. Edit.", 2002, pp. 2113-2116, vol. 41.
Demko et al., "An Expedient Route to the Tetrazole Analogues of a-Amino Acids", "Org. Lett.", 2002, pp. 2525-2527, vol. 4, No. 15.
Fisher et al., "5-Aroyltetrazoles", "J. Org. Chem.", 1959, pp. 1650-1654, vol. 24.
Janssens et al., "Synthetic 1,4-Disubstituted-I,4-dihydro-5H-tetrazol-5-Doneer ivatives of Fentanyl: Alfentanil (R 39209), a Potent, Extremely Short-Acting Narcotic Analgesic", "J. Med. Chem.", 1986, pp. 2290-2297, vol. 29.

(Continued)

*Primary Examiner* — Shobha Kantamneni
(74) *Attorney, Agent, or Firm* — Brian E. Davy; Bozicevic, Field & Francis LLP

(57) ABSTRACT

It has been discovered that inhibiting mitochondrial respiration in platelets reduces platelet activation or platelet aggregation. Certain heterocyclic compounds significantly reduced one or more platelet functions including clumping, sticking or platelet-stimulated clotting. Thus diseases or disorders mediated by inappropriately high levels of platelet activation or platelet aggregation can be treated by administering a therapeutically effective amount of a heterocyclic compound or nonheterocyclic mitochondrial inhibitor that significantly reduces one or more platelet functions including clumping, sticking or platelet-stimulated clotting, preferably in a reversible manner.

6 Claims, No Drawings

(56) References Cited

OTHER PUBLICATIONS

Kadaba et al., "Role of Protic and Dipolar Aprotic Solvents in Cycloaddition Reactions Involving Anionic 1,3-Dipoles. Action of Inorganic Azides on Imidoyl Chlorides", "J. Org. Chem.", 1976, pp. 1073-1075, vol. 41.

Mihina et al., "The Reaction of Nitriles With Hydrazoic Acid: Synthesis of Monosubstituted Tetrazoles", "J. Org. Chem.", 1950, pp. 1082-1092, vol. 15.

Pedersen, "The Preparation of Some N-Methyl-1.2.3-Triazoles", "Acta Chem. Scand.", 1959, pp. 888-892, vol. 13.

Schmidt et al., "Safe and fast tetrazole formation in ionic liquids", "Tetrahedron", 2007, pp. 492-496, vol. 63.

Shimada et al., "Synthesis and Gastric Antisecretory Activity of N-Cyano-N'-(phenyl-pyridinylmethyl)guanidine Derivatives", "Chem. Pharm. Bull.", 1984, pp. 4893-4906, vol. 32.

Verheyde et al., "Synthesis of Dendrimers Containing 1,3,4-Oxadiazoles", "J. Org. Chem.", 2001, pp. 4062-4064, vol. 66.

Wang et al., "Bromo-Directed N-2 Alkylation of NH-1,2,3-Triazoles: Efficient Synthesis of Poly-Substituted 1,2,3-Triazoles", "Org. Lett.", 2009, pp. 5490-5493, vol. 11, No. 23.

Wang et al., "General Solution to the Synthesis of N-2-Substituted 1,2,3-Triazoles", "Org. Lett.", 2010, pp. 4632-4635, vol. 12.

Zhu et al., "One-Pot Synthesis of 5-Substituted 1H-Tetrazoles from Aryl Bromides with Potassium Hexakis(cyano-kC)ferrate(4-) (K4[Fe(CN)6]) as Cyanide Source", "Helv. Chim. Acta.", 2009, pp. 171-175, vol. 92.

C.S. Ingalls, P. Somani, E.H. Freimer, "Inhibition of platelet aggregation by moxalactam and free N-methylthiotetrazole.", "Clinical Therapeutics", 1989, pp. 640-651, vol. 11, No. 5, Publisher: Elsevier, Published in: clinicaltherapeutics.com. (Abstract only has been submitted herewith.).

* cited by examiner

REDUCING PLATELET ACTIVATION, AGGREGATION AND PLATELET-STIMULATED THROMBOSIS OR BLOOD COAGULATION BY REDUCING MITOCHONDRIAL RESPIRATION

CROSS REFERENCE TO RELATED APPLICATIONS

This application claims benefit of Provisional Application 61/327,613 filed on Apr. 23, 2010.

FEDERALLY-SPONSORED RESEARCH OR DEVELOPMENT

This invention was made with Government support under contract GM017880 awarded by the National Institute of Health. The Government has certain rights in this invention.

BACKGROUND OF THE INVENTION

1. Field of the Invention

The invention is in the field of treatment and control of disorders and medical conditions associated with inappropriately high platelet activation or aggregation.

2. Description of the Related Art

Blood clotting and hemostasis are complex processes involving platelets, soluble clotting factors and tissue elements. Clotting function has been conceptually divided into platelet activity and clotting factor reactions. Platelets form an integral part of the body's capacity for hemostasis. Upon activation, platelets change shape, aggregate, and secrete their granular contents, resulting in the aggregation of platelets with each other and with non-platelet surrounding cells. The granular contents of platelets supply additional adhesion molecules, growth factors, coagulation enzymes and other specialized molecules instrumental in the process of blood coagulation and thrombus formation as well as the initiation of tissue growth and healing processes.

Many chronic and acute diseases are associated with inappropriately high platelet activity and thrombosis. A connection is also emerging between platelet activation and inflammation, particularly allergic inflammation (e.g., in asthma) and inflammation at the sites of atherosclerotic damage. See, for example: Rinder & Fitch, 1996, J Cardiovasc Pharmacol 27, Suppl. 1:S6 12 (investigating the role of complement components in activation of platelet and polymorphonuclear neutrophils by cardiopulmonary bypass); Palabrica et al., 1992, Nature 359, 848 851 (P-selectin mediates leukocyte adhesion to platelets in vivo, and the bound leukocytes promote fibrin deposition); Papayianni et al., 1995, Kidney Int 47, 1295 1302 (reduction of platelets reduces generation of immune modulator lipoxin A4 generation during experimental immune complex-mediated glomerulonephritis); Bazzoni et al., 1991, Haematologica 76, 491 499 (review describing the elaborate cross-talk between platelets and neutrophils in thrombotic and inflammatory diseases); and Kazura, 1989, J Lab Clin Med 114, 469 470 (editorial on the platelet-neutrophil interaction and modulation of the inflammatory response). Therefore, compounds that inhibit platelet activation may also be useful in the treatment or prevention of disorders involving inflammation.

There are a number of agents presently available that target platelet function, such as aspirin, which is an irreversible platelet inhibitor. In addition to the unwanted anticoagulation associated with overdosage, aspirin may cause life-threatening allergic reactions in sensitive individuals. Another platelet inhibiting agent is ticlopidine (Ticlid™, Roche Pharmaceuticals). However, because it requires the production of active metabolites to be effective, the effect of ticlopidine is delayed 24 to 48 hours and individuals lacking the appropriate cytochrome P450 enzymes necessary for the production of the active metabolites are resistant to its effects. Ticlopidine is also associated with the unwanted side effects of thrombotic thrombocytopenic purpura, a life-threatening condition, as well as nausea, abdominal pain, dyspepsia, diarrhea and skin rash. Clopidogrel (Plavix™, Bristol-Meyers Squibb/Sanofi Pharmaceuticals) is another platelet inhibitor that requires the generation of active metabolites for its therapeutic efficacy. Therefore, clopidogrel also has a delay of 24 to 48 hours for its effect. Clopidogrel is also associated with unwanted side effects such as thrombotic thrombocytopenia purpura as well as agranulocytopenia, both of which may be life-threatening conditions. In addition clopidogrel has been associated with rash, edema, hypertension, hypercholesterolemia, nausea, abdominal pain, dyspepsia, diarrhea, urinary tract infections, liver enzyme elevations and arthralgia. The platelet inhibitory agents Abciximab and c7E3 Fab (Reopro Abciximab™, manufacturer—Centocor B. V., distributor—Eli Lilly and Co.) are only available in a parenteral form. These drugs may in addition cause severe thrombocytopenia in addition to their desired anticoagulant effects. Both have a very long half-life and, therefore, complicate surgery that is sometimes required in the setting of life-threatening arterial occlusion (e.g., emergent cardiac surgery in the settings of myocardial infarction or aortic aneurism).

Eptifibatide (Integrilin™, COR Therapeutics, Inc., Key Pharmaceuticals Inc.) and Tirofiban (Aggrastat™, Merck and Co., Inc.) are additional platelet inhibitory agents that are only available in a parenteral form. Tirofiban may cause thrombocytopenia, coronary artery dissection, bradycardia and edema, as well as dizziness and vasovagal reactions. Eptifibatide may cause hypotension.

There are also antithrombotic agents which target the clotting factor based functions of coagulation. Examples include Heparin, Warfarin and Hirudin analogues. Heparin, a highly-sulfated glycosaminoglycan, is widely used as an injectable anticoagulant and as an anticoagulant surface coating on the inner surfaces of various experimental and medical devices such as test tubes and renal dialysis machines to prevent blood clotting. Heparin prevents the formation of clots and extension of existing clots within the blood. While heparin does not break down clots that have already formed (unlike tissue plasminogen activator), it allows the body's natural clot lysis mechanisms to work normally to break down clots that have formed. Heparin is generally used for anticoagulation in acute settings such as acute coronary syndrome, e.g., NSTEMI, Atrial fibrillation, Deep-vein thrombosis and pulmonary embolism, Cardiopulmonary bypass for heart surgery, and in ECMO circuits for extracorporeal life support. It has a distinct advantage over other agents in the acute setting due to its easy rapid reversibility with protamine sulfate. Heparin is given parenterally, as it is degraded when taken by mouth. Heparin may be injected intravenously or subcutaneously (under the skin). Intramuscular heparin injections (into muscle) are avoided because of the potential for forming hematomas. Because of its short biologic half-life of approximately one hour, heparin must be given frequently or as a continuous infusion. However, the use of low-molecular-weight heparin (LMWH) has allowed once-daily dosing, thus not requiring a continuous infusion of the drug. If long-term anticoagulation is required, heparin is often used only to commence anticoagulation therapy until the oral anticoagulant warfarin takes effect.

Hirudin, found naturally in the saliva of the medicinal leech, is an inhibitor of a specific factor in the soluble clotting factor cascade. Hirudin and its analogues have been used in medical cases requiring anticoagulation when other forms of anticoagulation are contraindicated or ineffective.

Warfarin (also known under the brand names Coumadin, Jantoven, Marevan, Lawarin, and Waran) is an anticoagulant that acts through inhibition of clotting factor synthesis. Despite its effectiveness, treatment with warfarin has several shortcomings. It has a relatively long half-life and many commonly used medications interact with warfarin, as do some foods. Its activity has to be monitored by frequent blood testing for the international normalized ratio (INR) to ensure an adequate yet safe dose is taken since its effects require synthesis of clotting factors. Warfarin is prescribed to people with an increased tendency for thrombosis or as secondary prophylaxis (prevention of further episodes) in those individuals that have already formed a blood clot (thrombus). Warfarin treatment may help prevent formation of future blood clots and reduce the risk of embolism (migration of a thrombus to a spot where it blocks blood supply to a vital organ).

In addition to the antithrombotic agents already on the market, there is still a need in the art for additional anticoagulant and platelet inhibitory agents for the treatment and prevention of diseases or disorders characterized by inappropriately elevated platelet activation, platelet aggregation and/or thrombosis. While these diseases may respond to anticoagulant therapy, they often require rapid surgical intervention and consequently the ability to rapidly reverse the anticoagulated state is highly advantageous.

SUMMARY OF THE INVENTION

Embodiments of the present invention provide methods for preventing or treating a disease or disorder mediated by inappropriately high levels of platelet activation or platelet aggregation and enumerated herein in a mammal, comprising administering to the mammal a therapeutically effective amount of a heterocyclic compound (an active agent) that significantly reduces one or more platelet functions including clumping, sticking or platelet-stimulated clotting, for example in an in vitro assay. In other embodiments any assay that permits a determination of the effect of a compound on one or more platelet functions that reflect a reduction in platelet aggregation or activation may be used may be used. In an embodiment the heterocyclic compound (HC) significantly reduces mitochondrial respiration in the platelets, preferably in a reversible manner. Examples of heterocyclic compounds for use in the present embodiments include those identified by Formula I and Formula II, and the compounds 2, 47, 48, 50, 51, 54, 72, 77, 78, 81, 84, 90, 91 and 99 with formulas corresponding to those in Table 1. In some embodiments these active agents are used the manufacture of a medicament for the prevention, delay of progression or treatment of a disease and disorder mediated by inappropriately high platelet activation or aggregation.

An embodiment is directed to the new compound 2-(2-(4-methylthiazol-5-yl)ethoxy)-2-oxoethyl)triphenylphosphonium bromide (49) or a pharmaceutically acceptable salt thereof.

Other embodiments are directed to an anticoagulant comprising heterocyclic active agents included in the group comprising heterocyclic compounds that significantly reduces one or more of platelet clumping, sticking or platelet-stimulated clotting in whole blood by at least a 10% change in baseline levels for each respective measurement, heterocyclic compounds of Formula I or Formula II, compounds 2, 47, 48, 50, 51, 54, 72, 77, 78, 81, 84, 90, 91 and 99 with formula corresponding to those in Table 1, or a pharmaceutically acceptable salt thereof.

Certain embodiments are directed to methods for reducing platelet activation and platelet aggregation in vitro by contacting the platelets with an amount of one or more of the above-described heterocyclic active agents. In another embodiment a medical device that comes into contact with blood, is coated with one or more of the above-described heterocyclic active agents.

Another embodiment is directed to a method of preventing blood clots, embolisms, thrombosis or other platelet aggregation disorder in a patient during and following a surgical procedure by (a) administering to the patient a therapeutically effective amount of one or more of the above-described heterocyclic active agents; (b) submitting the patient to a procedure such as percutaneous coronary interventions, stent placement, balloon angioplasty, coronary atherectomy, coronary endarterectomy, carotid endarterectomy, thrombolytic therapy, coronary or other vascular graft surgery, and dialysis that has a risk of causing inappropriately high levels of platelet activation or platelet aggregation; (c) discontinuing administering of the heterocyclic compound to the patient; and (d) allowing the amount of the heterocyclic compound in the patient's blood to decrease to a level below a therapeutically effective amount.

In another embodiment preventing or treating a disease or disorder mediated by inappropriately high levels of platelet activation or platelet aggregation in a mammal, is accomplished by administering a therapeutically effective amount of a compound that significantly reduces mitochondrial respiration in platelets.

Definitions

"Heterocyclic compounds" are neutral or charged molecules constituting covalently bonded cycles that have 3-10 atoms, at least one of which is a hetero atom. Heteroatoms include nitrogen, oxygen, sulfur, phosphorus and selenium. In one embodiment, the cycle comprises 5-6 atoms including at least two atoms that are heteroatoms. In other embodiments the heteroatoms are separated from one another by one atom in the cycle. In certain embodiments the heterocyclic inhibitors have two heteroatoms that are each capable of binding to metal ion centers. In some embodiments the heterocyclic inhibitors have one or more substituent groups, such as polar groups that modulate the water-solubility of the heterocyclic compound. "Organic Chemistry" by K. Peter C. Vollhardt and Neil E. Schore, Chapter 25, pages 1104-1130, Fourth Edition, W. H. Freeman and Company, New York, 2003.

By "open chain molecules with 1,3 heteroatoms" is meant certain linear or branched non-cyclic molecules with heteroatoms at the 1,3-disposition.

By "polar substituents" is meant certain polar groups on the heterocyclic compounds that confer additional water solubility on an active agent that might otherwise have low solubility in water. Such groups include carboxylic acids, carboxylic amides, amines, sulfides, sulfoxides, sulfonic acids, sulfonamides, alcohols, and ethers.

As used herein, an "active agent" is any compound that reduces one or more of the activities of platelet activation, aggregation or thrombosis in an assay that measures platelet activity such as platelet propensity for clumping, sticking or platelet-stimulated clotting in whole blood by at least a 10% change in baseline levels for each respective measurement. By "mitochondrial inhibitor" is meant a compound that significantly reduces mitochondrial respiration, by reducing mitochondrial oxygen consumption to levels below those necessary to support a platelet activation function, including platelet propensity for clumping, sticking or clotting as described and determined herein. The concentration of a compound to reduce the mitochondrial respiration to half of its maximum level (IC50) is used as an indication of its functional inhibitory activity.

A "heterocyclic mitochondrial inhibitor" of "HMI" is a mitochondrial inhibitor that is a heterocyclic compound.

As used herein "significantly reduces one or more platelet functions" means a change of at least about 10% in the baseline level for each respective platelet function measurement in the platelet function assay. For the in vitro whole blood assay used herein, a 10% increase in clumping, sticking or clotting time above baseline represents a significant reduction of the respective platelet function.

By "platelet function" is meant any function that indicates platelet activation or aggregation, including clumping, sticking or platelet-stimulated clotting.

As used herein, the term "platelet activation" refers to the process whereby a functionally resting platelet is stimulated to secrete one or more factors involved in thrombus formation or inflammation, or to aggregate. The term "platelet activation" is used herein to refer to the process whereby a platelet gains the expression of any one or more of these activities. The propensity of platelets to undergo activation may be measured through a variety of methods. Herein it has been measured by the propensity of platelets to clump together and subsequently stick to the walls of the test tube in an in vitro assay.

As used herein, the term "platelet aggregation" refers to the adhesion of activated platelets to one another that results in the formation of aggregates or clumps of activated platelets. The propensity for platelet aggregation is also proportional to clumping and sticking within the in vitro assay used herein.

As used herein blood coagulation means a complex process by which blood forms clots or thrombus. It is an important part of hemostasis (the cessation of blood loss from a damaged vessel), wherein a damaged blood vessel wall is covered by a platelet and fibrin-containing clot to stop bleeding and begin repair of the damaged vessel. Disorders of coagulation may lead to an increased risk of bleeding (hemorrhage) or clotting (thrombosis). Anticoagulation activity and anticoagulants reduce blood coagulation.

As used herein, the term "thrombosis" refers to the formation or development of a thrombus. Thrombosis is the formation of a blood clot (thrombus). When thrombosis occurs inside a blood vessel, obstructing the flow of blood through the circulatory system, tissue perfusion may be compromised resulting in irreversible tissue damage. When a blood vessel is injured, the body uses platelets and fibrin to form a blood clot. The first step in injured blood vessel repair (hemostasis) is prevention of loss blood loss. If that mechanism causes too much clotting, tissue perfusion may be compromised. If and the clot breaks free an embolus is formed which may occlude the circulation at a site distant from the site of clot formation. Thrombosis in a patient may be monitored by angiography, MRI or CAT scanning. "Reduced thrombosis" means either that there is no growth or increase in size of one or more thrombi, or that one or more thrombi have become smaller. The propensity of blood for thrombosis is measured by the time it takes blood or plasma to clot under standard laboratory conditions. In the HMA assay used herein, platelet induced clotting corresponds to the final clotting endpoint.

As used herein, the term "antithrombotic activity" refers to a compound that reduces thrombosis or the propensity of blood to undergo thrombosis or clot as defined above.

As used herein, the term "disease or disorder characterized by thrombosis" refers to a disease or disorder in which one or more aspects of the pathology is caused by the presence or formation of one or more thrombi.

The term "thrombosis associated with a surgical procedure" refers to the formation of one or more thrombi either during or following a surgical procedure, where such thrombi are clinically undesirable.

By "inappropriately high platelet activation or aggregation" is meant that the levels of platelet activation or aggregation are high enough to cause one of the enumerated disorders or unwanted blood clotting or coagulation. In some instances in medical practice, unwanted clotting and coagulation occur at the normal physiologic state, when platelet activation levels are not abnormally high. For instance, during bypass procedures or ECMO, patients will clot off the device unless they are anticoagulated to a state well outside the normal physiologic range. The methods of the present invention that prevent thrombosis also cover these instances where the platelet activations are physiologically normal, but the risk of clotting warrants suppression of platelet activation, either locally or systemically. Blood coagulation disorders that may be treated or prevented with the active compounds of the present invention are described below.

By "clinically undesirable" is meant that the thrombi pose a threat to the health or recovery of the individual.

A "therapeutically effective amount" is an amount that reduces or ameliorates a symptom of the disease. In the methods described herein, it will be understood that "treating" a disease encompasses not only improving the disease or its symptoms but also retarding the progression of the disease or ameliorating the disease. The art is replete with methods for measuring these parameters to enable a physician to individualize treatment for a particular patient; some of them are described below.

DETAILED DESCRIPTION

Seventeen specific heterocyclic compounds (HC) have been identified that are instantaneously able to reduce platelet activation or platelet aggregation in the in vitro assay, described herein, qualifying them as "active agents". All of these 17 HC active agents were also tested in an in vitro assay of mitochondrial respiration and all were in fact mitochondrial inhibitors, most of which were rapidly reversible. Certain embodiments are directed to methods for reducing inappropriately high levels of platelet activation or platelet aggregation in a mammal by administering effective amounts of one or more heterocyclic active agents including those of Formula I (tetrazoles) or Formula II (triazoles), or a mitochondrial inhibitor, that significantly reduces one or more platelet functions including clumping, sticking or platelet-stimulated clotting as defined herein.

Heterocyclic compounds that are active agents for the purpose of this invention may be readily be identified by screening in an in vitro assay for the ability to reduce platelet activation and/or aggregation in whole blood. As is described below, about ⅔ of the HC that were tested for the ability to reduce one or more platelet functions that are recognized indicia of platelet activation and/or aggregation (clumping, sticking or clotting) in the in vitro whole blood assay were "active agents." The assay described herein is very simple and rapid to perform, however any platelet function assay may be used. Since many HC may be expected to be active agents, it does not involve undue experimentation to identify other HC active agents besides those identified and described below. Similarly, known mitochondrial inhibitors may also be quickly screened in a platelet function assay such as that described below to determine the ability to inhibit a platelet function, and hence aggregation or activation in whole blood under physiologic conditions.

Certain further embodiments of the invention provide methods for preventing or treating a disease or disorder mediated by inappropriately high levels of platelet activation or platelet aggregation in a mammal, by administering a therapeutically effective amount of at least one heterocyclic compound identified as an active agent.

Many of the active HC that demonstrated the ability to reduce platelet activation, aggregation and/or clotting (active agents) were triazoles of Formula I, and thiazoles of Formula II as described below. One new HC (thiazole derivative, compound #49) was also discovered (FORMULA II, R1=methyl, R2=2-[(triphenylphosphoniumyl) acetyloxy]ethyl) that significantly reduced platelet activity or aggregation as measured by clumping, sticking and clotting in the in vitro whole blood assay described below. Certain embodiments are also directed to pharmaceutical formulations of active agents identified herein for therapeutic use.

In other embodiments, the active agents are applied to any portion of a medical device that contacts the blood, such as the inside wall of stents to prevent platelet aggregation.

Overview

Therapeutic control of platelet aggregation and coagulation are currently challenging clinical problems. All of the known therapeutic agents that inhibit coagulation work by inhibiting key enzyme pathways. While a number of drugs are available to inhibit platelet function through a variety of biochemical pathways, none have targeted respiration of platelet mitochondria, including the enzymes and Complexes I-V of their electron transport system. This is because the importance of mitochondrial function to platelet activity has not been appreciated, and because such inhibitors, if potent and able to distribute broadly to the tissues, would likely be quite toxic. Consequently, the discovery that significantly reducing mitochondrial respiration in platelets reduces activation or aggregation or clotting or all three, leads to an entirely new class of drugs for the prevention of unwanted platelet activation, aggregation and thrombosis.

Heterocyclic Mitochondrial Inhibitors

Certain heterocyclic compounds were selected for testing in a mitochondrial inhibition assay, described in detail in Example 1 Table 1. In this assay, mitochondria isolated from liver of tilapia (*Sarotheridon mossambica*) were incubated in the appropriate concentration of HC for 2 minutes at 0° C. The suspension of mitochondria and the HC were then injected into a respiration chamber, and the respirometer was allowed to stabilize for 1 minute before data collection. The mitochondrial respiration rate was measured at different concentrations for each HC. The percentage of mitochondrial inhibition was determined by comparing these rates to the respiration rate in the absence of the HC. Mitochondrial inhibition is presented in IC50. A weak inhibitor may still be a useful inhibitor, provided it is given at a high enough concentration (a large IC50 value).

Twenty-five HC were tested in the mitochondrial inhibition assay; all 25 HC tested inhibited mitochondrial respiration with IC50 values ranging from 5.4 mg/ml for compound 91 to 107.1 mg/ml for compound 72. See Table 4 in Example 2. HC that inhibited mitochondrial respiration are referred to herein as heterocyclic mitochondrial inhibitors (HMI). Of the 25 HMI identified, 17 were active in the platelet assays described below, and 8 compounds (47, 50, 51, 54, 72, 81, 90, and 91) were inactive in the platelet assays because they elicited only subthreshold responses for clumping sticking and clotting, as defined herein. Conversely, all of the HC that were "active agents" in the in vitro platelet assay on whole blood described below, did in fact significantly inhibit mitochondrial respiration.

Without being bound by theory, structural similarities of the HC to other known inhibitors of Complexes III and IV of the electron transport chain suggest that these entities are the main sites of interaction. Both complexes form part of the electron transport chain responsible for the energy metabolism of mitochondria.

Because the HMI were contemplated for therapeutic use in a mammal, seven of the 25 HMI compounds were tested for reversibility of mitochondrial inhibition. After exposure to an HMI, the mitochondria were pelleted out of solution by centrifugation at 10,000 g for 4 minutes at 0° C., resuspended in the respiration buffer, recentrifuged and resuspended once more, before they were monitored with an oxygen electrode. An HMI was considered "reversible" if the mitochondrial respiration rate after removing the inhibitor returned to greater than 75% of its value in the absence of inhibitor.

Six of the seven HC tested were reversible mitochondrial inhibitors (compounds 93, 94, 47, 83, 34, 48); only one was irreversible (compound 49). Reversibility was seen as soon as the measurements could be made (after about 4 minutes of washing and resuspending). A reversible inhibitor has the advantage of providing both positive and negative control over enzyme activity after the initial dose and consequently is the preferred therapeutic agent as will be discussed in more detail below. This result was unexpected and opens the door to the therapeutic use of reversible mitochondrial inhibitors for the diseases and disorders associated with unwanted or inappropriately high levels of platelet activation, aggregation and thrombosis.

It is important for therapeutic intervention that the platelet inhibitors act rapidly, which the HC active agents identified herein do, and inhibit mitochondria in a rapidly reversible manner which all the reversible inhibitors that were tested did.

Heterocyclic Mitochondrial Inhibitors that Reduce Platelet Aggregation, Sticking and Clumping A total of eighty-six compounds (see Table 1), of which eighty-one are heterocyclic compounds (HC), were tested in an in vitro assay that measures platelet clumping, sticking and platelet-stimulated clotting in whole blood, details of which are set forth in Example 2. Compounds 85, 86, 88, 89, and 102 in Table 1 are not HC, and none of them were active agents. Clumping and sticking are measures of platelet function. Prolonged clumping and sticking endpoints indicate impaired function. The clotting endpoint is a measure of coagulation cascade function triggered by platelet activation. Any platelet function that indicates platelet activation or aggregation may be monitored. As is explained above, the criterion for "significantly reducing one or more platelet functions" is a change of at least about 10% in the baseline level for each respective platelet function measurement in the platelet function assay. For the in vitro whole blood assay used herein, a 10% increase in clumping, sticking or clotting time above baseline represents a significant reduction of the respective platelet function. Of the 81 HC tested, 25 had been identified as heterocyclic mitochondrial inhibitors (HMI) as described above. Platelet function testing was conducted using the Hemostasis Mechanism Analyzer (HMA), which allows global testing of platelet and coagulation function. Unlike traditional platelet aggregation procedures, the HMA allows for simultaneous evaluation of the coagulation factor cascade along with evaluation of platelet function. The parameters of clumping, sticking and clotting were assessed in samples of human blood. 120% of baseline clotting time; 150% of baseline sticking time; and 150% of baseline clumping time were considered thresholds of activity. Testing was performed by adding three drops (~150 microliters) of citrated blood to a calcium/saline suspension of celite to which glass beads have been added. Normal platelets will undergo visible clumping, followed by "sticking" to the walls of the revolving tube. Finally, clotting occurs. Endpoints are determined visually in well-lighted, slowly revolving, almost horizontal tubes kept at 37° C. Details are set forth in Example 1.

Table 1 lists all the compounds that were studied in the instant application, including the chemical structures, IUPAC nomenclature and the sources or procedures of obtaining them.

TABLE 1

| Compound No. | Structure | IUPAC names | Source |
|---|---|---|---|
| 1 | 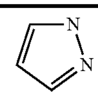 | 1H-pyrazole | Sigma-Aldrich |
| 2 | 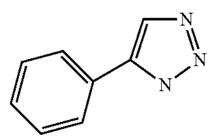 [SMILES: c1ccc(-c2cnn[nH]2)cc1] | 5-phenyl-1H-triazole | Reference 2 |
| 3 | 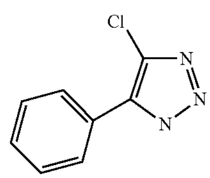 [SMILES: Clc1nn[nH]c1-c1ccccc1] | 4-chloro-5-phenyl-1H-triazole | Reference 3 |
| 5 | 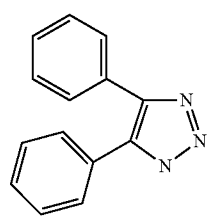 [SMILES: c1ccc(-c2nn[nH]c2-c2ccccc2)cc1] | 4,5-diphenyl-1H-triazole | Reference 4 |
| 8 | 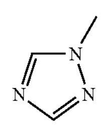 | 1-Methyl-1,2,4-triazole | Alfa Aesar |
| 9 | 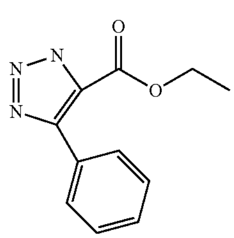 [SMILES: CCOC(=O)c1[nH]nnc1-c1ccccc1] | ethyl 4-phenyl-1H-triazole-5-carboxylate | Reference 5 |
| 10 | 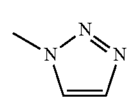 | 1-methyltriazole | Reference 6 |
| 11 | 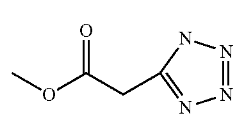 | methyl 2-(1H-tetrazol-5-yl)acetate | EXAMPLE 4 |

TABLE 1-continued

| Compound No. | Structure | IUPAC names | Source |
|---|---|---|---|
| 13 | 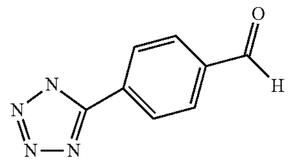 [SMILES: O=Cc1ccc(-c2nnn[nH]2)cc1] | 4-(1H-tetrazol-5-yl)benzaldehyde | Reference 7 |
| 15 | 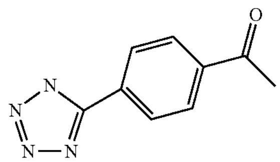 | 1-[4-(1H-tetrazol-5-yl)phenyl]ethanone | Reference 8 |
| 17 | 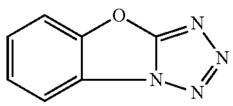 [SMILES: c1ccc2c(c1)oc1nnnn12] | tetrazolo[5,1-b][1,3]benzoxazole | Reference 9 |
| 18 | 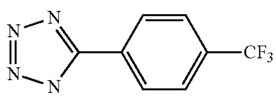 [SMILES: FC(F)(F)c1ccc(-c2nnn[nH]2)cc1] | 5-[4-(trifluoromethyl)phenyl]-1H-tetrazole | Reference 8 |
| 20 | 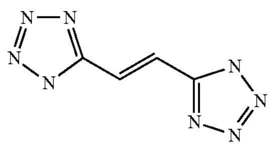 [SMILES: C(=C\c1nnn[nH]1)/c1nnn[nH]1] | 5-[(E)-2-(1H-tetrazol-5-yl)vinyl]-1H-tetrazole | Reference 10 |
| 21 | 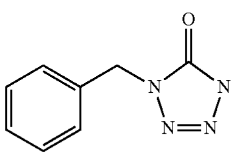 [SMILES: O=c1[nH]nnn1Cc1ccccc1] | 4-benzyl-1H-tetrazol-5-one | Reference 11 |
| 22 | 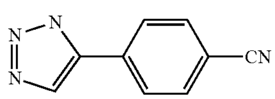 [SMILES: N#Cc1ccc(-c2cnn[nH]2)cc1] | 4-(1H-triazol-5-yl)benzonitrile | Reference 12 |
| 23 | 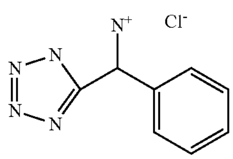 [SMILES: [Cl-] ; [NH3+]C(c1ccccc1)c1nnn[nH]1] | [phenyl(1H-tetrazol-5-yl)methyl]ammonium chloride | Reference 13 |
| 24 | 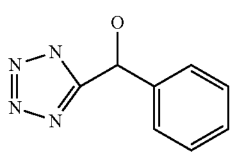 [SMILES: OC(c1ccccc1)c1nnn[nH]1] | phenyl(1H-tetrazol-5-yl)methanol | Reference 14 |
| 25 | 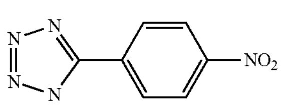 [SMILES: O=[N+]([O-])c1ccc(-c2nnn[nH]2)cc1] | 5-(4-nitrophenyl)-1H-tetrazole | Reference 1 |
| 26 | 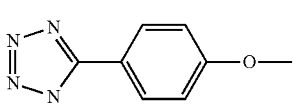 | 5-(4-methoxyphenyl)-1H-tetrazole | Reference 1 |

TABLE 1-continued

| Compound No. | Structure | IUPAC names | Source |
|---|---|---|---|
| 27 | 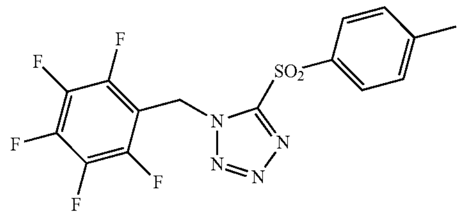 | 1-[(2,3,4,5,6-pentafluorophenyl)methyl]-5-(p-tolylsulfonyl)tetrazole | Reference 15 |
| 28 | 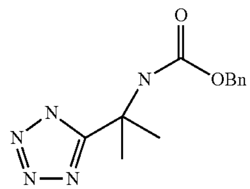 [SMILES: CC(C)(NC(=O)OCc1ccccc1)c1nnn[nH]1] | benzyl N-[1-methyl-1-(1H-tetrazol-5-yl)ethyl)carbamate | Reference 16 |
| 29 | 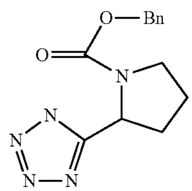 [SMILES: O=C(OCc1ccccc1)N1CCCC1c1nnn[nH]1] | benzyl 2-(1H-tetrazol-5-yl)pyrrolidine-1-carboxylate | Reference 16 |
| 32 | 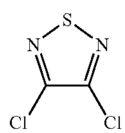 | 3,4-dichloro-1,2,5-thiadiazole | Sigma-Aldrich |
| 33 | 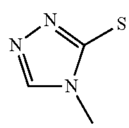 | 4-methyl-1,2,4-triazole-3-thiol | Sigma-Aldrich |
| 34 | 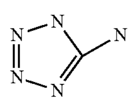 | 1H-tetrazol-5-amine | Sigma-Aldrich |
| 35 | 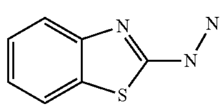 [SMILES: NNc1nc2ccccc2s1] | 1,3-benzothiazol-2-ylhydrazine | Sigma-Aldrich |
| 36 | 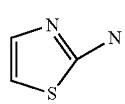 | thiazol-2-amine | Sigma-Aldrich |
| 37 | 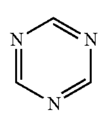 | 1,3,5-triazine | Sigma-Aldrich |
| 38 | 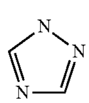 | 1H-1,2,4-triazole | Sigma-Aldrich |
| 39 | 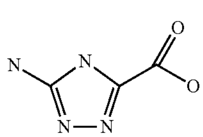 | 5-amino-4H-1,2,4-triazole-3-carboxylic acid | Sigma-Aldrich |

TABLE 1-continued

| Compound No. | Structure | IUPAC names | Source |
|---|---|---|---|
| 40 | 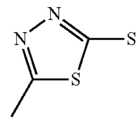 | 5-methyl-1,3,4-thiadiazole-2-thiol | Sigma-Aldrich |
| 41 | 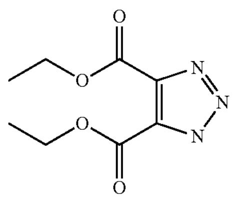 | diethyl 1H-triazole-4,5-dicarboxylate | Reference 17 |
| 42 | 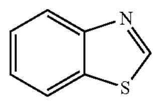 | 1,3-benzothiazole | Sigma-Aldrich |
| 43 | 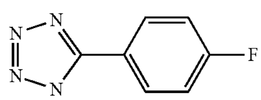 | 5-(4-fluorophenyl)-1H-tetrazole | Reference 18 |
| 44 | 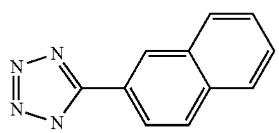 [SMILES: c1ccc2cc(-c3nnn[nH]3)ccc2c1] | 5-(2-naphthyl)-1H-tetrazole | Reference 1 |
| 45 | 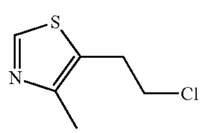 | 5-(2-chloroethyl)-4-methyl-thiazole | Sigma-Aldrich |
| 46 | 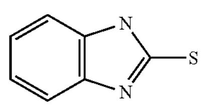 | 1H-benzimidazole-2-thiol | Sigma-Aldrich |
| 47 | 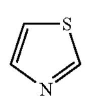 | Thiazole | Sigma-Aldrich |
| 48 | 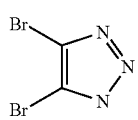 | 4,5-dibromo-1H-triazole | Reference 19 |
| 49 | 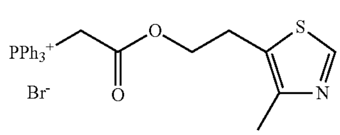 | [2-[2-(4-methylthiazol-5-yl)ethoxy]-2-oxo-ethyl]-triphenyl-phosphonium bromide | EXAMPLE 3 |
| 50 | L-ergothioneine | (2S)-3-(2-thioxo-1,3-dihydroimidazol-4-yl)-2-(trimethylammonio)propanoate | Sigma-Aldrich |

TABLE 1-continued

| Compound No. | Structure | IUPAC names | Source |
|---|---|---|---|
| 51 | D-ergothioneine | (2R)-3-(2-thioxo-1,3-dihydroimidazol-4-yl)-2-(trimethylammonio)propanoate | Example 3 |
| 52 | 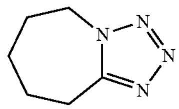 | 6,7,8,9-tetrahydro-5H-tetrazolo[1,5-a]azepine | Sigma-Aldrich |
| 53 | 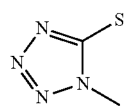 | 1-methyltetrazole-5-thiol | Sigma-Aldrich |
| 54 | 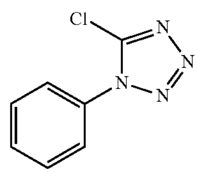 [SMILES: Clc1nnnn1-c1ccccc1] | 5-chloro-1-phenyl-tetrazole | Sigma-Aldrich |
| 55 | 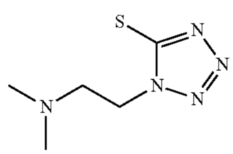 | 1-(2-dimethylaminoethyl)tetrazole-5-thiol | Sigma-Aldrich |
| 56 | 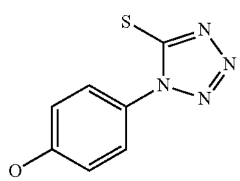 [SMILES: Oc1ccc(-n2nnnc2S)cc1] | 4-(5-sulfanyltetrazol-1-yl)phenol | Sigma-Aldrich |
| 57 | 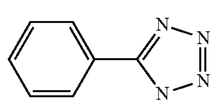 [SMILES: c1ccc(-c2nnn[nH]2)cc1] | 5-phenyl-1H-tetrazole | Sigma-Aldrich |
| 58 | 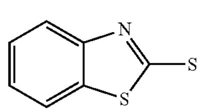 | 1,3-benzothiazole-2-thiol | Sigma-Aldrich |
| 59 | 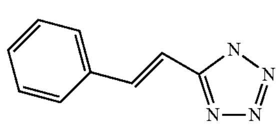 [SMILES: C(=C\c1nnn[nH]1)/c1ccccc1] | 5-[(E)-styryl]-1H-tetrazole | Reference 1 |
| 60 | 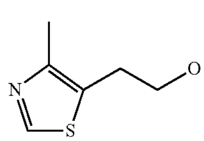 | 2-(4-methylthiazol-5-yl)ethanol | Sigma-Aldrich |

TABLE 1-continued

| Compound No. | Structure | IUPAC names | Source |
|---|---|---|---|
| 61 | 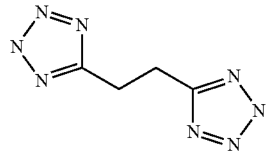 [SMILES: C(Cc1nn[nH]n1)c1nn[nH]n1] | 5-[2-(2H-tetrazol-5-yl)ethyl]-2H-tetrazole | DTP Open Repository (NCI/NIH) |
| 62 | 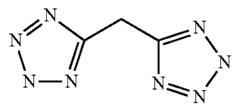 [SMILES: C(c1nn[nH]n1)c1nn[nH]n1] | 5-(2H-tetrazol-5-ylmethyl)-2H-tetrazole | DTP Open Repository (NCI/NIH) |
| 63 | 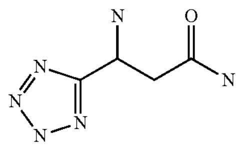 [SMILES: NC(=O)CC(N)c1nn[nH]n1] | 3-amino-3-(2H-tetrazol-5-yl)propanamide | DTP Open Repository (NCI/NIH) |
| 64 | 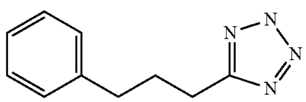 [SMILES: c1ccc(CCCc2nn[nH]n2)cc1] | 5-(3-phenylpropyl)-2H-tetrazole | DTP Open Repository (NCI/NIH) |
| 65 | 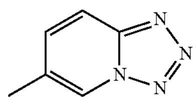 | 6-methyltetrazolo[1,5-a]pyridine | DTP Open Repository (NCI/NIH) |
| 66 | 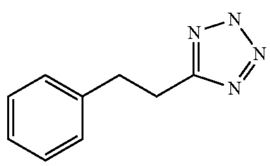 [SMILES: c1ccc(CCc2nn[nH]n2)cc1] | 5-phenethyl-2H-tetrazole | DTP Open Repository (NCI/NIH) |
| 67 | 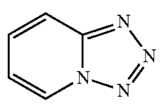 | tetrazolo[1,5-a]pyridine | DTP Open Repository (NCI/NIH) |
| 68 | 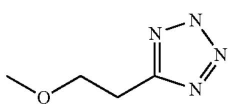 | 5-(2-methoxyethyl)-2H-tetrazole | DTP Open Repository (NCI/NIH) |
| 69 | 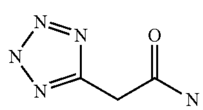 | 2-(2H-tetrazol-5-yl)acetamide | DTP Open Repository (NCI/NIH) |
| 70 | 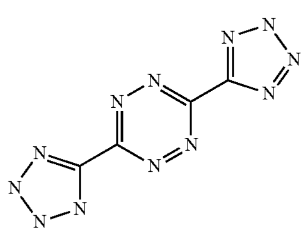 [SMILES: N1=C(c2nnc(-c3nn[nH]n3)nn2)NNN1] | 3-(2,3-dihydro-1H-tetrazol-5-yl)-6-(2H-tetrazol-5-yl)-1,2,4,5-tetrazine | DTP Open Repository (NCI/NIH) |
| 71 | 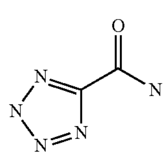 | 2H-tetrazole-5-carboxamide | DTP Open Repository (NCI/NIH) |

TABLE 1-continued

| Compound No. | Structure | IUPAC names | Source |
|---|---|---|---|
| 72 | 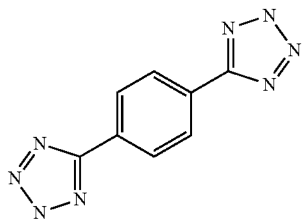 [SMILES: c1cc(-c2nn[nH]n2)ccc1-c1nn[nH]n1] | 5-[4-(2H-tetrazol-5-yl)phenyl]-2H-tetrazole | DTP Open Repository (NCI/NIH) |
| 73 | 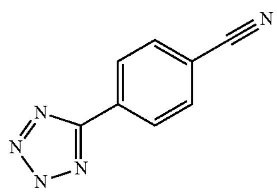 [SMILES: N#Cc1ccc(-c2nn[nH]n2)cc1] | 4-(2H-tetrazol-5-yl)benzonitrile | DTP Open Repository (NCI/NIH) |
| 74 | 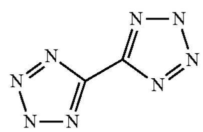 | 5-(2H-tetrazol-5-yl)-2H-tetrazole | DTP Open Repository (NCI/NIH) |
| 75 | 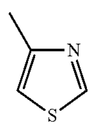 | 4-methylthiazole | Sigma-Aldrich |
| 76 | 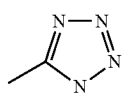 | 5-methyl-1H-tetrazole | Sigma-Aldrich |
| 77 | 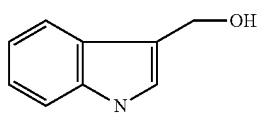 [SMILES: OCc1c[nH]c2ccccc12] | 1H-indol-3-ylmethanol | Sigma-Aldrich |
| 78 | 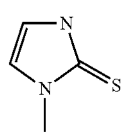 | methimazole 3-methyl-1H-imidazole-2-thione | Sigma-Aldrich |
| 80 | 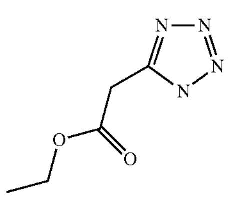 | ethyl 2-(1H-tetrazol-5-yl)acetate | Sigma-Aldrich |
| 81 | 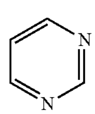 | pyrimidine | Sigma-Aldrich |
| 82 | 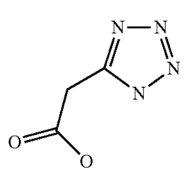 | 2-(1H-tetrazol-5-yl)acetic acid | Sigma-Aldrich |

TABLE 1-continued

| Compound No. | Structure | IUPAC names | Source |
|---|---|---|---|
| 83 | 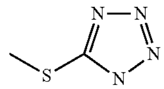 | 5-methylsulfanyl-1H-tetrazole | Sigma-Aldrich |
| 84 | 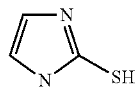 | 1H-imidazole-2-thiol | Sigma-Aldrich |
| 85 | 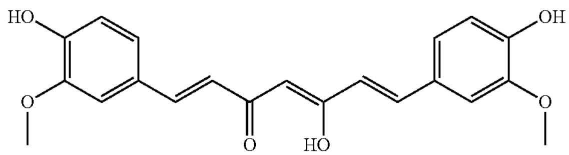 [SMILES: COc1cc(/C=C/C(=O)/C=C(O)/C=C/c2ccc(O)c(OC)c2)ccc1O] | (1E,4Z,6E)-5-hydroxy-1,7-bis(4-hydroxy-3-methoxyphenyl)hepta-1,4,6-trien-3-one (curcumin) | Sigma-Aldrich |
| 86 | 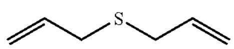 | 3-allylsulfanylprop-1-ene | Sigma-Aldrich |
| 87 | 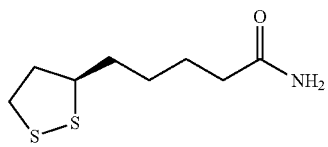 [SMILES: NC(=O)CCCC[C@@H]1CCSS1] | 5-[(3R)-dithiolan-3-yl]pentanamide (lipoamide) | Sigma-Aldrich |
| 88 | 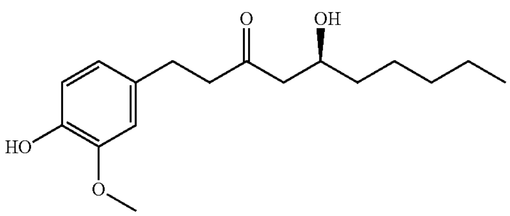 [SMILES: CCCCC[C@H](O)CC(=O)CCc1ccc(O)c(OC)c1] | (5S)-5-hydroxy-1-(4-hydroxy-3-methoxyphenyl)decan-3-one (gingerol | Sigma-Aldrich |
| 89 | 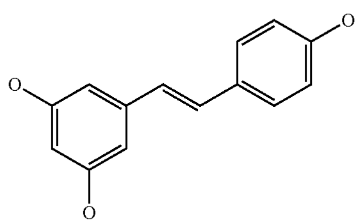 [SMILES: Oc1ccc(/C=C/c2cc(O)cc(O)c2)cc1] | 5-[(E)-2-(4-hydroxyphenyl)vinyl]benzene-1,3-diol (resveratrol) | Sigma-Aldrich |
| 90 | 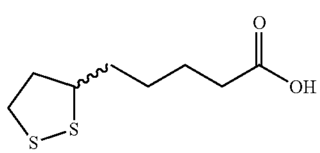 [SMILES: O=C(O)CCCCC1CCSS1] | lipoic acid (LA) (racemate) 5-[(3R or 3S)-dithiolan-3-yl]pentanoic acid | Sigma-Aldrich |
| 91 | 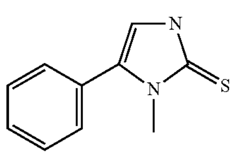 | 5-phenylmethimazole 3-methyl-4-phenyl-1H-imidazole-2-thione | Santa Cruz Biotech |
| 92 | 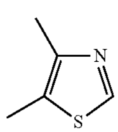 | 4,5-dimethylthiazole | Sigma-Aldrich |
| 93 | 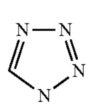 | tetrazole | Reference 21 |

TABLE 1-continued

| Compound No. | Structure | IUPAC names | Source |
|---|---|---|---|
| 94 | 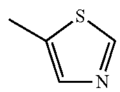 | 5-methylthiazole | Sigma-Aldrich |
| 99 | 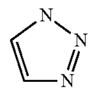 | 1H-triazole | Sigma-Aldrich |
| 102 | 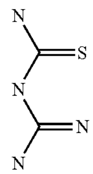 | carbamimidoylthiourea | Sigma-Aldrich |

References for Table 1.
1. Alterman, M.; Hallberg, A. *J. Org. Chem.* 2000, 65, 7984-7989.
2. Wang, X.; Sidhu, K.; Campbell, S.; et al. *Org. Lett.* 2009, 11, 5490-5493.
3. Kuang, C.; Kong, L. *Faming Zhuanli Shenqing.* 2010, CN 101786993 A 20100728.
4. Butler, R. N.; Hanniffy, J. M.; Stephens, J. C.; et al. *J. Org. Chem.* 2007, 73, 1354-1364.
5. Amantini, D.; Fringuelli, F.; Piermatti, O.; et al. *J. Org. Chem.* 2005, 70, 6526-6529.
6. Pedersen, C. *Acta Chem. Scand.* 1959, 13, 888-892.
7. Das, B.; Reddy, C. R.; Kumar, D. N.; *Synlett.* 2010, 3, 391-394.
8. Zhu, Y.; Ren, Y.; Cai, C. *Helv. Chim. Acta.* 2009, 92, 171-175.
9. Kadaba, P. K. *J. Org. Chem.* 1976, 41, 1073-1075.
10. Schmidt, B.; Meid, D.; Kieser, D. *Tetrahedron.* 2007, 63, 492-496.
11. Janssens, F.; Torremans, J.; Janssen, P. A. K. *J. Med. Chem.* 1986, 29, 2290-2297.
12. Andersen, J.; Bolvig, S.; Liang, X.; *Synlett.* 2005, 19, 2941-2947.
13. Shimada, K.; Fujisaki, H.; Oketani, K.; et al. *Chem. Pharm. Bull.* 1984, 32, 4893-4906.
14. Fisher, B. E.; Tomson, A. J.; Horwitz, J. P. *J. Org. Chem.* 1959, 24, 1650-1654.
15. Demko, Z. P.; Sharpless, K. B. *Angew. Chem. Int. Edit.* 2002, 41, 2110-2113.
16. Demko, Z. P.; Sharpless, K. B. *Org. Lett.* 2002, 4, 2525-2527.
17. Yasuda, S.; Imura, K.; Okada, Y.; et al. PCT Int. Appl. 2003, WO 2003064400 A1 20030807.
18. Verheyde, B.; Dehaen, W. *J. Org. Chem.* 2001, 66, 4062-4064.
19. Wang, X.; Zhang, L.; Krishnamurthy, D.; et al. *Org. Lett.* 2010, 12, 4632-4635.
20. Brown, S. E.; Ross, M. F.; Sanjuan-Pla, A.; et al. *Free Radical Bio. Med.* 2007, 42, 1766-1780.
21. Mihina, J. S.; Herbst, R. M. *J. Org. Chem.* 1950, 15, 1082-1092.

Of the 81 heterocyclic compounds tested, twenty-six of them met the criteria for "active agents." The 26 most active heterocyclic compounds in the three in vitro whole blood assays are listed in Table 3, according to three indicia, clumping, sticking and clotting. Twelve heterocyclic compounds were active for all 3 indicia. Platelet data for 47 of the 86 compounds tested is set forth in Table 4. Tables 3-4 are set forth in the Results section of Example 2.

Most of the active heterocyclic agents fell into two groups: tetrazoles of Formula I, and thiazoles of Formula II. Other HC tested that met the criteria for active agents are compounds 2, 48, 77, 78, and 84 with formula corresponding to those in Table 1.

There are two main classes of active heterocyclic agents. The first are tetrazoles of FORMULA I:

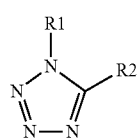

FORMULA I

Active compounds also include variations of FORMULA I wherein:
R1 is a member selected from the group comprising hydrogen, or ethoxycarbonylmethyl, or 4-hydroxyphenyl, and R2 is a member selected from the group comprising
hydrogen
hydroxyl
4-formylphenyl
4-acetylpheny
alpha-hydroxylbenzyl
amino
sulfhydryl
5-tetrazolylmethyl
phenethyl
aminocarbonyl
5-tetrazolyl
methyl
ethoxycarbonylmethyl
carboxymethyl
methylmercapto The second class of active agents are thiazoles having FORMULA II.

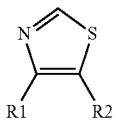

FORMULA II

R1 is a member selected from the group comprising hydrogen, methyl and 1,3-butadiene-1,4-diyl (together with R2), and R2 is a member selected from the group comprising hydrogen methyl 1,3-butadiene-1,4-diyl (together with R1)

2-[(triphenylphosphoniumyl)acetyloxy]ethyl 2-hydroxyethyl

Certain embodiments are directed to (1) pharmaceutical formulations of one or more of the active agents or pharmaceutically acceptable salts thereof for therapeutic use in a mammal, preferably a human, (2) to methods for preventing or reducing inappropriately high levels of platelet activation or platelet aggregation or thrombosis in a mammal, or (3) to treating or preventing a disease or disorder associated with inappropriately high levels of platelet activation or platelet aggregation or thrombosis by administering a therapeutically effective amount of (1) one or more of the 26 heterocyclic active agents listed in Table 3 (entitled: Active compounds in platelet function testing), (2) a heterocyclic compound that reduces one or more indicia of platelet activity in the whole blood in vitro assay described herein or any substantially equivalent assay, or (3) any mitochondrial inhibitor that significantly reduces mitochondrial respiration in platelets.

Diseases or disorders that may be treated or prevented by administration of one or more active agents, include acute myocardial infarction, ischemic stroke, angina pectoris, acute coronary syndromes, TIA (transient ischemic attacks, or acute cerebrovascular syndromes), heart failure, chest pain of ischemic etiology, syndrome X, thromboembolism, pulmonary hypertension, diabetes mellitus, peripheral vascular disease, venous thrombosis of any vessel, deep vein thrombosis, arterial thrombosis of any vessel, catheter thrombotic occlusion or reocclusion, stable and unstable angina, transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation, autoimmune disorders, diseases of a congenital and or genetic nature, cardiovascular diseases, arterial thrombosis of any vessel, catheter thrombotic occlusion, reocclusion; stable angina; unstable angina; transient ischemic attack; cerebrovascular disease; peripheral vascular disease; placental insufficiency; thrombosis subsequent to or associated with a surgical procedure; and thrombosis associated with atrial fibrillation.

Other diseases that may be treated or prevented by administration of one or more active agents include genetic hypercoagulable conditions such as Factor V Leiden mutation, prothrombin gene mutation, antithrombin deficiency, Protein C deficiency, Protein S deficiency, Heparin Cofactor II Deficiency, Tissue Factor Pathway Inhibitor Deficiency, elevated lipoprotein a, homocysteinemia, Factor XII deficiency, elevated factor VIII levels, Plasminogen deficiency, increased plasminogen activator inhibitor. Sometimes inappropriately high levels of platelet activation or aggregation may be acquired as a result of other conditions, and these too may be treated with the methods and pharmaceutical formulations of the present invention. Such acquired conditions may be associated with: overproduction of antiphospholipid antibodies, heparin-induced thrombocytopenia, Malignancy, Nephrotic syndrome, myeloproliferative disorders, Behcet's syndrome, microangiopathic hemolytic anemia which includes disseminated intravascular coagulopathy, thrombotic thrombocytopenic purpura and hemolytic uremic syndrome, pregnancy, oral contraceptive use, obesity, general anesthesia,immobility, varicose veins, infection, infusion of prothrombin complex concentrates treatment related to L-Asparaginase or Mitomycin.

Other embodiments are directed to the newly discovered compound 49 and salts thereof, and pharmaceutical formulations thereof.

Preferred active agents for use in the various embodiments are reversible mitochondrial inhibitors, as these will have fewer adverse side effects if they should reach unintended target tissues. In many cases the active agents will be administered intravenously. Active agents that are the most useful therapeutically are most likely the small, charged molecules because they have greater aqueous solubility and consequently better distribution within the bloodstream. Furthermore small, charged molecules are expected to distribute less broadly into the tissues due to their decreased ability to cross membrane barriers. Small charged molecules are also more likely to be excluded from the central nervous system as they do not easily cross the blood brain barrier (BBB).

Larger molecules, whether charged or uncharged are more likely to interact with other enzymes (i.e. not mitochondrial enzymes) and proteins in the blood and in surrounding tissues, and to that extent they could interfere with those biochemical pathways. However, in some embodiments the large active agents for use in the present methods are formulated so that they do not easily leave the blood stream or cross the BBB. Uncharged molecules whether large or small are more likely to penetrate the blood brain barrier, and consequently harm biochemical pathways in the nervous system.

Therapeutically Effective Doses

Administration of the active agents in accordance with the present invention may be continuous or intermittent, depending, for example, upon the recipient's physiological condition, whether the purpose of the administration is therapeutic or prophylactic, and other factors known to skilled practitioners. Administration may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors may be readily determined by the clinician employing animal models or other test systems which are well known to the art.

Whenever a compound is referred to as therapeutically effective to treat or prevent a condition associated with elevated platelet activation, aggregation or blood coagulation, a corresponding salt of the compound is also intended.

In some embodiments one or more of the HC active agents will be administered as the only anticoagulants, however they may also be administered together with other types of anticoagulants like warfarin, heparin or hirudin, for example. In some embodiments the active agents may be formulated into depot preparations for slow release.

The active agents in tables 1, 2 and 3 were effective over a broad range of concentrations. It is noted that some of the highly active heterocyclic compounds (HC) required fairly large amounts. When one extrapolates the amounts of the active agents that were used to reduce platelet clumping, sticking and clotting (amounts of from about 0.1 to 1.0 mg/ml to whole blood in the in vitro assays) to account for the human blood volume of about 5 liters, many of the high activity compounds would be administered in amounts of about 500 mg to about 5 g to an adult human subject. While such large doses may not be therapeutically useful for long term administration, they could be valuable tools in a crisis situation for a relatively short period of time and could be infused to yield high enough local concentrations to be instantaneously effective, but upon dilution within the entire circulation would not compromise coagulation function at distant anatomical sites. Such infusion would permit the control of an unwanted thrombus in the heart while not interfering with wound healing at a distant site for instance. Such agents could be used to treat conditions before or during certain surgical procedures such as percutaneous coronary interventions, stent placement, balloon angioplasty, coronary atherectomy, coronary endarterectomy, carotid endarterectomy, thrombolytic therapy, coronary or other vascular graft surgery, and dialysis. There are also many acute problems of inappropriately high platelet activity and/or thrombosis that could be treated with high dose HC, such as transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation. Inhibitors of platelet activity may provide therapeutic and preventive benefits for each of these diseases or disorders. A person of skill in the art will be able to identify situations where use of agents with high activity are indicated, despite the higher doses.

Unpublished results showed that mitochondrial inhibition with tetrazole resulted in elevated levels of hydrogen peroxide. Various experimental models of Parkinson's disease and other maladies have implicated mitochondrial dysfunction and excessive Reactive Oxygen Species (ROS) as possible contributors. Fortunately it is routine in the art to screen mitochondrial inhibitors or indeed any platelet inhibitor for hydrogen peroxide production in vitro, to select active agents that are suitable for long term administration as long as the production of hydrogen peroxide is not excessive.

Although reversible mitochondrial inhibitors are preferred, they may still be associated with some toxicity if they produce toxic levels of hydrogen peroxide, which could limit their use for long-term administration. Toxicity from hydrogen peroxide is related not so much to the amount of the inhibitor administered as it is to the type and strength of the inhibition. Therefore, before a mitochondrial inhibitor or active agent is administered to a subject, it should be tested in vitro to determine the amount of hydrogen peroxide it produces at any given concentration. Active agents that produce acceptable levels of hydrogen peroxide would be preferred, especially for long term use for treating chronic conditions such as coronary artery disease, myocardial infarction and associated angina, cerebrovascular disease and peripheral vascular diseases.

Active agents that reversibly inhibit mitochondria are preferred. An important result of the mitochondrial inhibition experiments is that all but one of the active heterocyclic mitochondrial inhibitors that were tested were reversible. Reversible heterocyclic mitochondrial inhibitors will therefore be washed out over time once administration is stopped, typically through the kidneys in the urine. The reversible HMI, even though relatively small molecules, will also be metabolized over time.

Certain surgical procedures place a patient at risk of forming blood clots, embolisms, etc. An embodiment of the invention includes a method of preventing blood clots, embolisms, thrombosis or other disorders associated with inappropriately high platelet aggregation, by treating a patient that is to be subjected to certain surgical procedures by: (a) administering a therapeutically effective amount of an active agent; (c) submitting the patient to a procedure selected from the group comprising percutaneous coronary interventions, stent placement, balloon angioplasty, coronary atherectomy, coronary endarterectomy, carotid endarterectomy, thrombolytic therapy, coronary or other vascular graft surgery, and dialysis, (d) discontinuing the administering of the active agent; and (e) allowing the amount of the active agent in the patient's blood to decrease to a level below a therapeutically effective amount. Other diseases or conditions that may be treated like this include tissue salvage following surgical or accidental trauma, or reconstructive surgery and mechanical-induced platelet activation that is for example caused by cardiopulmonary bypass resulting in microthromboembolism, platelet refractoriness, and thrombocytopenia; said thrombotic complications resulting from shunt occlusion are associated with procedures of renal dialysis or plasmapheresis.

An intravascular thrombus may result from pathological disturbances of hemostasis, or by the rupture of atherosclerotic plaques. Platelet adhesion and aggregation are critical events in intravascular thrombosis. Activated under conditions of high shear blood flow in diseased vessels or by the release of mediators from other circulating cells and damaged endothelial cells lining the vessel, platelets and other cells accumulate at a site of vessel injury to form a thrombus, and recruit more platelets to the developing thrombus. The thrombus may grow to sufficient size to block off arterial blood vessels. Thrombi may also form in areas of stasis or slow blood flow in veins. Venous thrombi may easily detach portions of themselves, creating emboli that travel through the circulatory system. This process may block other vessels, such as pulmonary arteries as occurs in pulmonary embolism or embolic stroke. Thus, arterial thrombi cause serious disease by local blockade, whereas the morbidity and mortality associated with venous thrombi arise primarily after distant blockade, or embolization. Conditions associated with pathological thrombus formation include venous thromboembolism, thrombophlebitis, deep vein thrombosis, arterial embolism, coronary and cerebral arterial thrombosis, unstable angina, myocardial infarction, stroke, transient ischemic attack, cerebral embolism, renal embolism and pulmonary embolism.

Disorders associated with inappropriately high platelet activation, platelet aggregation or thrombosis include certain autoimmune disorders, cardiovascular diseases and hematological disorders, including treating or preventing acute myocardial infarction, ischemic stroke, angina pectoris, acute coronary syndromes, TIA (transient ischemic attacks, or acute cerebrovascular syndromes), heart failure, chest pain of ischemic etiology, syndrome X, thromboembolism, pulmonary hypertension, diabetes mellitus, peripheral vascular disease, deep vein thrombosis, arterial thrombosis of any vessel, catheter thrombotic occlusion, reocclusion; stable angina; unstable angina; peripheral vascular disease; placental insufficiency; thrombosis subsequent to or associated with a surgical procedure; and thrombosis associated with atrial fibrillation. Inflammation associated with wound healing, atherosclerosis or allergy caused by elevated platelet activation or aggregation may also be treated according to the methods of the present invention. Surgical procedures associated with a risk of thrombosis include aortocoronary bypass surgery; coronary angioplasty; stent placement; and insertion of prosthetic heart valves.

Pharmaceutical Formulations and Preferred Routes of Administration

Aqueous solubility is important since blood constitutes an aqueous environment. Compounds that are soluble in water have the best chance of being delivered to the platelets. Routes of administration include injection (e.g., subcutaneous, intradermal, intravenous, intralymphatic, intraarticular, intramuscular, intraperitoneal), by continuous infusion, sustained release from implants, alimentary administration (oral, rectal), mucosal absorption (nasal spray, and pulmonary nebulizer, etc. Routine experimentation will determine the optimal formulations, doses and routes of administration. The dosage of the active compound may depend on a variety of factors, such as mode of administration, homeothermic species, age and/or individual condition. Preferred dosages for the active ingredients according to the present invention are therapeutically effective dosages that may be determined by routine experimentation. The active agents may be administered once per day or multiple times per day, or they may be infused. Some conditions may be optimally treated by local administration such as pulmonary embolism, cardiac canula for thrombi within the cardiac atria.

The active agents may be administered as pharmaceutically acceptable salts or in the form of bases. The therapeutic agents may be present in amorphous form or in crystalline forms, including hydrates and solvates. Preferably, the pharmaceutical compositions comprise a therapeutically effective amount of the active agent. Pharmaceutically acceptable salts of the therapeutic agents described herein include those salts derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate salts. Other acids, such as oxalic, while not in themselves pharmaceutically acceptable, may be employed in the preparation of salts useful as intermediates in obtaining pharmaceutically acceptable acid addition salts.

Salts derived from appropriate bases include alkali metal (e.g., sodium and potassium), alkaline earth metal (e.g., magnesium), ammonium and $N^+(C_{1-4}alkyl)_4$ salts. This invention also envisions the quaternization of any basic nitrogen-containing groups of the therapeutic agents disclosed herein. Water or oil-soluble or dispersible products may be obtained by such quaternization.

The therapeutic agents of the present invention are also meant to include all stereochemical forms of the therapeutic agents (i.e., the R and S configurations for each asymmetric center). Therefore, single enantiomers, racemic mixtures, and diastereomers of the therapeutic agents are within the scope of the invention. Also within the scope of the invention are steric isomers and positional isomers of the therapeutic agents. The therapeutic agents of the present invention are also meant to include compounds which differ only in the presence of one or more isotopically enriched atoms. For example, therapeutic agents in which one or more hydrogens are replaced by deuterium or tritium, or the replacement of one or more carbons by $^{13}C$- or $^{14}C$-enriched carbon are within the scope of this invention.

However, the pharmaceutical compositions may be administered parenterally, by inhalation spray, topically, rectally, nasally, buccally, vaginally or via an implanted reservoir. Sterile injectable forms of the pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The pharmaceutical compositions employed in the present invention may be orally administered in any orally acceptable dosage form, including, but not limited to, solid forms such as capsules and tablets. In the case of tablets for oral use, carriers commonly used include microcrystalline cellulose, lactose and corn starch. Lubricating agents, such as magnesium stearate, are also typically added. When aqueous suspensions are required for oral use, the active ingredient may be combined with emulsifying and suspending agents. If desired, certain sweetening, flavoring or coloring agents may also be added.

The pharmaceutical compositions employed in the present invention may also be administered by nasal aerosol or inhalation. Such pharmaceutical compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Should topical administration be desired, it may be accomplished using any method commonly known to those skilled in the art and includes but is not limited to incorporation of the pharmaceutical composition into creams, ointments, or transdermal patches.

For certain medical indications it may be useful to administer the compounds in liposomes, in which case compounds with relatively low water solubility could be used.

The pharmaceutical compositions according to the invention may be prepared in any manner known per se to make a composition comprising a therapeutically effective amount of the pharmacologically active compound, alone or in combination with one or more pharmaceutically acceptable carriers. Typical oral formulations include tablets, capsules, syrups, elixirs and suspensions. Typical injectable formulations include solutions and suspensions. The pharmaceutical compositions may be employed for the treatment of conditions mediated by platelet aggregation.

The typical pharmaceutically acceptable carriers for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, buffers, preservatives, antioxidants, lubricants, flavoring agents, and the like commonly used in pharmaceutical formulations.

The pharmaceutical preparations consist of from about 0.1% to 90%, preferably of from about 1% to about 80%, of the active compounds. Pharmaceutical preparations for enteral or parenteral administration are, for example, in unit dose forms, such as coated tablets, tablets, capsules or suppositories and also ampoules. These are prepared in any manner known in the art, for example using conventional mixing, granulation, coating, and solubulizing or lyophilizing processes. Thus, pharmaceutical preparations for oral use may be obtained by combining the active compounds with solid excipients, if desired granulating a mixture which has been obtained, and, if required or necessary, processing the mixture or granulate into tablets or coated tablet cores after having added suitable auxiliary substances.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts may be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malonic, mesylic, adipic, lactic, tartaric, salkylic, methanesulfonic, 2-hydroxyethanesulfonic, toluenesulfonic, benzenesulfonic, camphorsulfonic, and ethanesulfonic acids. The pharmaceutically acceptable base addition salts may be formed with metal or organic counterions and include, but are not limited to, alkali metal salts such as sodium or potassium; alkaline earth metal salts. Other salts such as hydrochlorides, hydrobromides, mesylates, sulfates, acetates, tartrates, etc., are also contemplated in this invention. Preferred counterions are monovalent ions such as $NH_4^+$, sodium, lithium, potassium, chloride, bromide, bisulfate, and mesylate, with sodium, potassium, chloride and mesylate being most preferred due to ease of manufacture, stability, and physiological tolerance.

The active, agents of the present invention may be combined with other therapeutic agents, e.g., each at an effective therapeutic dose as reported in the art. Such therapeutic agents include hirudin and its analogues, heparin, warfarin, t-PA, urokinase, streptokinase, aspirin, ticlopidine, clopidogrel, abciximab, eptifibatide and tirofiban, anti-hypertensive agents and anti-diuretics.

Furthermore, the actual dose and schedule may vary depending on whether the compositions are administered in combination with other pharmaceutical compositions, or depending on interindividual differences in pharmacokinetics, drug disposition, and metabolism.

EXAMPLES

Example 1

Isolation of Mitochondria

Mitochondria were isolated from the liver of tilapia (*Sarotheridon mossambica*). The fish were purchased from a commercial source, killed by concussion, and stored on ice for less than 1 hour. The livers were dissected, and then minced on an ice-cooled glass plate in approximately six volumes of pH=7.4 buffer containing $KH_2PO_4$ (10 mM), sucrose (250 mM), EDTA (0.5 mM), and fatty acid-free bovine serum albumin (1 mg/ml). The liver was pulverized using a Dounce homogenizer before it was centrifuged at 500 g for 10 minutes at 0° C. The supernatant was then filtered through glass wool to remove any loose lipid material. The obtained filtrate was centrifuged at 10,000 g for 10 minutes at 0° C. to sediment a crude mitochondrial pellet. The gold-colored mitochondrial material of the pellet was then resuspended in fresh pH=7.4 buffer (5 ml), homogenized, and centrifuged at 10,000 g for 10 minutes at 0° C. This resuspension procedure was repeated two additional times to remove any non-mitochondrial material. The final mitochondrial pellet was resuspended in approximately 2 ml of pH=7.5 buffer containing Tris-HCl (50 mM), NaCl (100 mM), EDTA (0.1 mM), and DTT (1 mM). The suspension was stored on ice for less than 24 hours before use. Using the Bradford assay[1] with bovine serum albumin as a standard, the protein content of the suspension was measured to vary between 0.4 and 1.1 mg/ml depending upon sample preparation.

Inhibition of Mitochondrial Respiration

Mitochondrial respiration rates were measured with a Clark oxygen electrode in a closed glass chamber. The respiration chamber was filled with an air-saturated pH=7.0 respiration buffer (1.2 ml) containing $KH_2PO_4$ (100 mM), $MgCl_2$ (500 mM), glycine (500 mM), HEPES (50 mM), ADP (0.17 mM), malic acid (6.7 mM), and succinic acid (6.7 mM). The temperature of the chamber was kept constant at 20° C. using a circulating water bath, and its contents were magnetically stirred.

A suspension of mitochondria (100 μL) was incubated in the appropriate concentration of inhibitor in a pH=7.0 solution of $KH_2PO_4$ (100 mM) for 2 minutes at 0° C. The suspension of mitochondria and the inhibitor were then injected into the respiration chamber via syringe, and the respirometer was allowed to stabilize for 1 minute before data collection commenced. The oxygen concentration of the cell was recorded five times per second for 3 minutes with data acquisition software (WinDAQ). Respiration rates were averaged over this time period and subtracted by the background rate of oxygen consumption by the electrode. For each inhibitor, the mitochondrial respiration rate was measured at different inhibition incubation concentrations. The percentage of mitochondrial inhibition was then determined by comparing these rates to the respiration rate in the absence of inhibitor.

The half maximal inhibitory incubation concentration ($IC_{50}$) for a compound was calculated by fitting a linear or sigmoidal equation to the percentage inhibition versus incubation concentration of inhibitor. For a mitochondrial preparation containing 0.50 mg/ml protein, tetrazole had an $IC_{50}$ value of 31.5 mg/ml. Inhibition by tetrazole was measured on each fresh batch of mitochondria. The $IC_{50}$ values of other inhibitors were then multiplied by a normalization factor of measured tetrazole inhibition to correct for differences in mitochondrial activity amongst different mitochondrial preparations.

Reversibility Measurements

A suspension of mitochondria (100 μL) was incubated in the appropriate volume of inhibitor in a pH=7.0 solution of $KH_2PO_4$ (100 mM) for 2 minutes at 0° C. to give the $IC_{50}$ concentration. The mitochondria were then pelleted out of solution by centrifugation at 10,000 g for 4 minutes at 0° C., resuspended in the respiration buffer described above (1.2 ml), and centrifuged and resuspended once more, before they were monitored with the oxygen electrode. An inhibitor was considered "reversible" if the mitochondrial respiration rate after removing the inhibitor returned to greater than 75% of its value in the absence of inhibitor.

TABLE 2

Mitochondria Inhibition Results

| Compound No. | IC$_{50}$ (mg/ml) | Reversible? |
|---|---|---|
| 93 | 31.5 | Yes |
| 94 | 23.5 | Yes |
| 75 | 40.6 | N/A |
| 92 | 50.9 | N/A |
| 47 | 21.3 | Yes |
| 83 | 14.5 | Yes |
| 76 | 12.6 | N/A |
| 82 | 11.8 | N/A |
| 80 | 100 | N/A |
| 71 | 36.3 | N/A |
| 72 | 107.1 | N/A |
| 81 | 51.5 | N/A |
| 50 | 86 | N/A |
| 51 | 93.8 | N/A |
| 84 | 17.3 | N/A |
| 78 | 25.7 | N/A |
| 91 | 5.4 | N/A |
| 90 | 37.1 | N/A |
| 77 | 82.8 | N/A |
| 99 | 104 | N/A |
| 53 | 27.5 | N/A |
| 54 | 12.5 | N/A |
| 49 | 8.8 | No |
| 34 | 8.5 | Yes |
| 48 | 30 | Yes |

Example 2

Platelet Function Testing was Conducted Using the Hemostasis Mechanism Analyzer (HMA)
Overview The HMA allows global testing of platelet and coagulation function. Unlike traditional platelet aggregation procedures, the HMA allows for simultaneous evaluation of the coagulation factor cascade along with evaluation of platelet function. The following parameters were assessed in samples of human blood: % of baseline clotting time; % of baseline sticking time; and % of baseline clumping time. Testing was performed by adding three drops (~150 microliters) of citrated blood to a calcium/saline suspension of celite to which glass beads have been added. Normal platelets will undergo visible clumping, followed by "sticking" to the walls of the revolving tube. Finally, clotting occurs. Endpoints are determined visually in well-lighted, slowly revolving, almost horizontal tubes kept at 37° C. Clumping and sticking are measures of platelet function. Prolonged clumping and sticking endpoints indicate impaired function. The clotting endpoint is a measure of coagulation cascade function triggered by platelet activation.
Materials and Methods Special supplies Timer (measures in seconds), Automatic pipettes and tips, 5-50 microliters adjustable, 100-1000 microliters adjustable, Test tubes: 12×75 mm and 13×100 mm, Parafilm, Caps for 12×75 tubes,
Instrumentation
Hemostasis Mechanism Analyzer (HMA)

Temperature (displayed on side of instrument) must be checked prior to each use. The acceptable range is 37+/−1° C. Rotation of the specimen should be maintained at 15+/−1 RPM. Rocking of the specimen should be maintained at 15+/−1 cycles per minute.

Heat Block

Specimens and reagents must be maintained at 37+/−1° C. Glass beads were 0.45-0.50 mm, an acceptable source is VWR #48300-431 (Propper Solid glass beads, Propper order #030001)

Celite 289 (Manville Products Corp., P.O. Box 5108, Denver, Colo. 80217)

Lyophilized reagent tubes—Celite 289

10-15 glass beads and 50 microliters of an additive solution made by suspending 160 mg Celite 289 in 8 ml DI water are added to a 12×75 mm test tube. The tube and contents are frozen and lyophilize until dry (a minimum of 4 hours). The final contents of the tube include 10-15 glass beads and 1 mg of celite. The tube is capped with parafilm and stored indefinitely at room temperature.

CaCl$_2$, 0.025 M (Stable one year at 2-8° C. unless contaminated)

Add 3.67 gm CaCl$_2$.2H$_2$O to a 1 liter volumetric flask. Fill to the 1 liter mark with distilled water, and mix to dissolve. As a quality measure, determine the osmolality of the solution. It should be 73-77 mOsm/Kg. The osmolality may be low if the CaCl$_2$.2H$_2$O has adsorbed additional water. If the osmolality is low, calculate the additional amount of CaCl$_2$.2H$_2$O needed as follows:

Grams additional CaCl$_2$.2H$_2$O needed=[(75×3.67)/(measured osmolality)]−3.67

Add the calculated amount of additional CaCl$_2$2H$_2$O needed, and mix to dissolve. Again, determine the osmolality to verify that it is now within range. Adjust again if necessary.

Once the appropriate CaCl$_2$.2H$_2$O concentration is attained, add 7 gm NaCl to the solution and mix to dissolve. Determine the osmolality, which should now be between 290-305 mOsm/Kg. The osmolality may be low if the NaCl has adsorbed water. If the osmolality is not within these limits, calculate the additional amount of NaCl needed as follows:

Grams additional NaCl needed=[(298−75)/(actual osmolality−75)]×7−7

Add the calculated amount of additional NaCl needed and mix to dissolve. Verify that the osmolality is within range and adjust as necessary. Once the appropriate osmolality has been reached, transfer the reagent to a glass bottle, label as Isotonic CaCl$_2$, 0.025M and store refrigerated.

NaCl, 0.9% (Sodium Chloride for Irrigation, USP)

CaCl2/NaCl working solution (stable one year at 2-8° C. unless contaminated)

Prepare as follows:

| | |
|---|---|
| Isotonic CaCl2, 0.025M | 200 ml |
| NaCl, 0.9% pH = 7.5 with HEPES buffer | 700 ml |

Mix the isotonic CaCl2 and pH=7.5 HEPES buffered NaCl 0.9% and transfer the mixed solution to a glass bottle, label as CaCl$_2$/NaCl (2 parts+7 parts) mixture and store refrigerated.

Inhibitor Solution

A stock solution of each inhibitor to be tested is made by dissolving a known quantity of each inhibitor in pH=7.5 HEPES buffered NaCl 0.9% solution to yield a stock solution. The stock solution is then diluted with additional pH=7.5 HEPES buffered NaCl 0.9% solution and used to make CaCl$_2$/NaCl working solution with the required inhibitor dosage. The CaCl$_2$/NaCl working solution containing inhibitor is labeled Inhibitor Solution and should be made fresh daily.

Specimen Collection and Preparation

Two Blue-Tops, 3 ml Draw each (1 Part 3.2% Citrate Plus 9 Parts Blood) are Required.

Specimens should be obtained from normal volunteer donors who are not taking any platelet-inhibiting medications. The minimum required volume is two 3-ml blue top tubes of blood. They should be drawn by trauma-free venipuncture or via an in-dwelling line cleared with a minimum of 15-20 cc of blood. The tubes should not be filled with more or less than the designated volume or errors will occur due to alterations in the blood/anticoagulant ratio. After drawing the blood, the tubes should be mixed gently by inversion 4-5 times. Other than this gentle inversion, agitation should be avoided. Excessive mixing/agitation may impair platelet function significantly.

Transfer the Blood to 5 ml Plastic Syringes Immediately.

After mixing the collection tube by inversion, the blood should be immediately transferred to a 5 ml plastic syringe. If immediate transfer cannot be made, the blood should be mixed by 2-3 inversions immediately before transferring. To transfer the blood, remove plunger and protective tip from syringe. Hold parafilm against luer tip of syringe, and decant specimen from tube into barrel of syringe. Place the plunger in position at base of barrel, tilt syringe tip up, and release pressure on parafilm to vent syringe. Slowly advance the plunger while holding the luer tip pointing upwards until all air is expelled from the syringe barrel. Wipe any spilled blood from the exterior of the syringe, parafilm the luer tip, and place the syringe horizontally in a 37° C. heat block or incubator.

HMA Testing

Prepare and Prewarm the Following Reagents and Supplies:

Fill two 13×100 mm test tubes with CaCl$_2$/NaCl and prewarm to 37° C.

Fill one 12×75 mm test tube with NaCl 0.9% and prewarm to 37° C.

Supplies: Lyophilized Celite 289 tubes, and Inhibitor Solution.

Perform Testing Between 45-150 Minutes Post-Collection.

The specimen must be warmed and maintained at 37° C. for accurate testing. After the specimen has been brought to the appropriate temperature, mix the specimen by rolling the syringe rapidly between the palms of the hands at least 30 times, keeping the syringe horizontal. This provides adequate mixing even in the absence of a mixing bubble. Discard the first 1-2 drops of blood before proceeding.

Testing Procedure with Celite 289:

Add 450 microliters Inhibitor Solution or CaCl$_2$/NaCl mix as required to a prewarmed lyophilized celite 289 tube. Add 3 drops blood and start timer. Record endpoints as determined visually by observing platelet clumping, sticking and clotting. The endpoints are defined as follows:

Clumping: Platelets begin to adhere to each other and with the celite forming visible clumps. The clumps do not yet stick to the walls of the tube. The endpoint is called when the clumps are approximately the same size as the glass beads.

Sticking: Platelet/celite clumps adhere to the walls of the tube and are pulled towards the left side of the tube and carried around out of sight.

Clotting: Clotting is recorded when a clot forms within the sample tube.

Calculations:

Recorded times for clotting, sticking and clumping are divided by the corresponding times in the absence of inhibitor and multiplied by 100 to yield a % of baseline time. The absolute inhibitor quantity present in the tube during testing is divided by the volume of whole blood (150 microliters) present in the tube during testing to yield an inhibitor dosage relative to whole blood.

The Nominal base was set at 100 percent and there was a control for every expt. Some nominal baselines were repeated and it was discovered that there was variability of 15-20% between the first and second measurements. Therefore, the thresholds for clumping and sticking assays are a minimum of 150% of the baseline. That for the clotting assay is set at 120% of the baseline.

Results:

TABLE 3

Active compounds in platelet function testing

| Clumping | Sticking | Clotting | Active in any one of clumping, sticking or clotting | Active in all three indicia of clumping sticking and clotting |
|---|---|---|---|---|
| 74 | 74 | 74 | 2 | 34 |
| 83 | 83 | 83 | 13 | 53 |
| 76 | 76 | 15 | 15 | 62 |
| 82 | 82 | 13 | 24 | 71 |
| 92 | 92 | 49 | 34 | 74 |
| 53 | 53 | 82 | 42 | 75 |
| 49 | 34 | 34 | 48 | 78 |
| 34 | 48 | 92 | 49 | 80 |
| 48 | 62 | 78 | 53 | 82 |
| 2 | 80 | 93 | 56 | 83 |
| 71 | 71 | 62 | 60 | 92 |
| 78 | 93 | 71 | 62 | 93 |
| 93 | 78 | 80 | 66 | |
| 80 | 60 | 53 | 71 | |
| 60 | 66 | 56 | 74 | |
| 42 | 75 | 75 | 75 | |
| 62 | 94 | 84 | 76 | |
| 66 | | 77 | 77 | |
| 24 | | | 78 | |
| 75 | | | 80 | |
| 94 | | | 82 | |
| | | | 83 | |
| | | | 84 | |
| | | | 92 | |
| | | | 93 | |
| | | | 94 | |

TABLE 4

Results of platelet function testing, including all the active compounds

| Compound No. | | % clump time increase | % stick time increase | % clot time increase |
|---|---|---|---|---|
| 74 | 5-(2H-tetrazol-5-yl)-2H-tetrazole Dosage (mg/ml) | | | |
| | 5 | 2293 | 1852 | 542 |
| | 3.3 | 441 | 413 | 190 |

TABLE 4-continued

Results of platelet function testing, including all the active compounds

| Compound No. | | % clump time increase | % stick time increase | % clot time increase |
|---|---|---|---|---|
| | 2.7 | 255 | 225 | 145 |
| | 2 | 145 | 157 | 128 |
| | 0.67 | 110 | 114 | 108 |
| | 0 | 100 | 100 | 100 |
| 83 | 5-methylsulfanyl-1H-tetrazole | | | |
| | Dosage (mg/ml) | | | |
| | 6.7 | 1384 | 1040 | 297 |
| | 5 | 584 | 512 | 191 |
| | 3.3 | 167 | 157 | 127 |
| | 0 | 100 | 100 | 100 |
| 76 | 5-methyl-1H-tetrazole | | | |
| | Dosage (mg/ml) | | | |
| | 6.7 | 1231 | 983 | 301 |
| | 3.3 | 209 | 217 | 120 |
| | 0.67 | 129 | 125 | 91 |
| | 0 | 100 | 100 | 100 |
| 82 | 2-(1H-tetrazol-5-yl)acetic acid | | | |
| | Dosage (mg/ml) | | | |
| | 5 | 755 | 601 | 217 |
| | 3.3 | 240 | 222 | 137 |
| | 0 | 100 | 100 | 100 |
| 53 | 1-methyltetrazole-5-thiol | | | |
| | Dosage (mg/ml) | | | |
| | 6.7 | 292 | 265 | 160 |
| | 5 | 185 | 176 | 132 |
| | 3.3 | 124 | 117 | 117 |
| | 0 | 100 | 100 | 100 |
| 48 | 4,5-dibromo-1H-triazole | | | |
| | Relative Dosage (Saturated Solution) | | | |
| | 0.7 | 276 | 247 | 111 |
| | 0.5 | 194 | 190 | 102 |
| | 0.3 | 132 | 147 | 102 |
| | 0.1 | 102 | 108 | 105 |
| | 0 | 100 | 100 | 100 |
| 34 | 1H-tetrazol-5-amine | | | |
| | Relative Dosage (Saturated Solution) | | | |
| | 0.7 | 271 | 254 | 162 |
| | 0.5 | 204 | 175 | 136 |
| | 0.3 | 138 | 123 | 109 |
| | 0 | 100 | 100 | 100 |
| 62 | 5-(2H-tetrazol-5-ylmethyl)-2H-tetrazole | | | |
| | Dosage (mg/ml) | | | |
| | 6.7 | 242 | 231 | 140 |
| | 5 | 170 | 164 | 122 |
| | 3.3 | 136 | 132 | 105 |
| | 0 | 100 | 100 | 100 |
| 71 | 2H-tetrazole-5-carboxamide | | | |
| | Dosage (mg/ml) | | | |
| | 6.7 | 236 | 205 | 137 |
| | 5 | 171 | 153 | 122 |
| | 3.3 | 126 | 116 | 112 |
| | 0 | 100 | 100 | 100 |
| 80 | ethyl 2-(1H-tetrazol-5-yl)acetate | | | |
| | Dosage (mg/ml) | | | |
| | 6.7 | 207 | 209 | 133 |
| | 5 | 143 | 141 | 121 |
| | 3.3 | 107 | 104 | 110 |
| | 0 | 100 | 100 | 100 |
| 92 | 4,5-dimethylthiazole | | | |
| | Dosage (mg/ml) | | | |
| | 23.3 | 717 | 546 | 162 |
| | 11.7 | 224 | 211 | 126 |
| | 6.7 | 195 | 179 | 106 |
| | 3.3 | 176 | 171 | 101 |
| | 0.7 | 112 | 118 | 100 |
| | 0 | 100 | 100 | 100 |

TABLE 4-continued

Results of platelet function testing, including all the active compounds

| Compound No. | | % clump time increase | % stick time increase | % clot time increase |
|---|---|---|---|---|
| 60 | 2-(4-methylthiazol-5-yl)ethanol Dosage (mg/ml) | | | |
| | 6.7 | 192 | 182 | 115 |
| | 5 | 158 | 155 | 110 |
| | 3.3 | 136 | 135 | 104 |
| | 0.7 | 108 | 103 | 100 |
| | 0 | 100 | 100 | 100 |
| 68 | 5-(2-methoxyethyl)-2H-tetrazole Dosage (mg/ml) | | | |
| | 6.7 | 186 | 175 | 129 |
| | 3.3 | 100 | 114 | 107 |
| | 0.67 | 100 | 110 | 108 |
| | 0 | 100 | 100 | 100 |
| 42 | 1,3-benzothiazole Relative Dosage (Saturated Solution) | | | |
| | 1.8 | 173 | 145 | 103 |
| | 1.4 | 153 | 136 | 106 |
| | 0.9 | 110 | 101 | 100 |
| | 0.2 | 106 | 97 | 102 |
| | 0 | 100 | 100 | 100 |
| 66 | N-(2,4-difluorophenyl)-1H-triazole-5-carboxamide Relative Dosage (Saturated Solution) | | | |
| | 0.7 | 162 | 171 | 112 |
| | 0.5 | 141 | 155 | 111 |
| | 0.3 | 127 | 129 | 101 |
| | 0.1 | 105 | 108 | 98 |
| | 0 | 100 | 100 | 100 |
| 24 | phenyl(1H-tetrazol-5-yl)methanol Dosage (mg/ml) | | | |
| | 6.7 | 160 | 143 | 116 |
| | 5 | 156 | 152 | 113 |
| | 3.3 | 126 | 124 | 105 |
| | 0.7 | 109 | 105 | 96 |
| | 0 | 100 | 100 | 100 |
| 61 | 5-[2-(2H-tetrazol-5-yl)ethyl]-2H-tetrazole Relative Dosage (Saturated Solution) | | | |
| | 3.1 | 141 | 134 | 119 |
| | 2.4 | 111 | 118 | 111 |
| | 0 | 100 | 100 | 100 |
| 41 | diethyl 1H-triazole-4,5-dicarboxylate Relative Dosage (Saturated Solution) | | | |
| | 0.7 | 139 | 135 | 113 |
| | 0.5 | 119 | 112 | 108 |
| | 0.3 | 105 | 101 | 103 |
| | 0 | 100 | 100 | 100 |
| 67 | tetrazolo[1,5-a]pyridine Relative Dosage (Saturated Solution) | | | |
| | 1.3 | 135 | 128 | 110 |
| | 1.0 | 127 | 115 | 106 |
| | 0.6 | 112 | 110 | 102 |
| | 0 | 100 | 100 | 100 |
| 65 | 6-methyltetrazolo[1,5-a]pyridine Relative Dosage (Saturated Solution) | | | |
| | 0.7 | 134 | 137 | 107 |
| | 0.6 | 112 | 114 | 97 |
| | 0.4 | 97 | 101 | 101 |
| | 0 | 100 | 100 | 100 |
| 43 | 5-(4-fluorophenyl)-1H-tetrazole Relative Dosage (Saturated Solution) | | | |

TABLE 4-continued

Results of platelet function testing, including all the active compounds

| Compound No. | | % clump time increase | % stick time increase | % clot time increase |
|---|---|---|---|---|
| | 5.2 | 131 | 121 | 102 |
| | 3.9 | 100 | 103 | 104 |
| | 0 | 100 | 100 | 100 |
| 49 | [2-[2-(4-methylthiazol-5-yl)ethoxy]-2-oxo-ethyl]-triphenyl-phosphonium bromide Relative Dosage (Saturated Solution) | | | |
| | 0.7 | 130 | 146 | 217 |
| | 0.5 | 136 | 146 | 208 |
| | 0.3 | 147 | 150 | 169 |
| | 0.1 | 117 | 132 | 148 |
| | 0 | 100 | 100 | 100 |
| 52 | 6,7,8,9-tetrahydro-5H-tetrazolo[1,5-a]azepine Dosage (mg/ml) | | | |
| | 6.7 | 130 | 131 | 117 |
| | 5 | 143 | 138 | 112 |
| | 3.3 | 115 | 120 | 105 |
| | 0 | 100 | 100 | 100 |
| 8 | 1-methyl-1,2,4-triazole Dosage (mg/ml) | | | |
| | 6.7 | 130 | 121 | 105 |
| | 5 | 121 | 118 | 105 |
| | 3.3 | 105 | 98 | 104 |
| | 0 | 100 | 100 | 100 |
| 54 | 5-chloro-1-phenyl-tetrazole Relative Dosage (Saturated Solution) | | | |
| | 0.6 | 127 | 113 | 95 |
| | 0.5 | 96 | 98 | 103 |
| | 0 | 100 | 100 | 100 |
| 9 | ethyl 4-phenyl-1H-triazole-5-carboxylate Relative Dosage (Saturated Solution) | | | |
| | 1.6 | 127 | 124 | 99 |
| | 1.2 | 102 | 109 | 95 |
| | 0 | 100 | 100 | 100 |
| 18 | 5-[4-(trifluoromethyl)phenyl]-1H-tetrazole Dosage (mg/ml) | | | |
| | 6.7 | 127 | 106 | 106 |
| | 0 | 100 | 100 | 100 |
| 56 | 4-(5-sulfanyltetrazol-1-yl)phenol Relative Dosage (Saturated Solution) | | | |
| | 2.9 | 125 | 114 | 122 |
| | 2.2 | 114 | 103 | 117 |
| | 1.5 | 109 | 105 | 112 |
| | 0.3 | 100 | 105 | 105 |
| | 0 | 100 | 100 | 100 |
| 78 | 1-methyl-1,3-dihydro-2H-imidazole-2-thione Dosage (mg/ml) | | | |
| | 23.3 | 216 | 203 | 156 |
| | 11.7 | 132 | 118 | 123 |
| | 6.7 | 124 | 101 | 110 |
| | 0 | 100 | 100 | 100 |
| 26 | 5-(4-methoxyphenyl)-1H-tetrazole Dosage (mg/ml) | | | |
| | 6.7 | 122 | 118 | 102 |
| | 0 | 100 | 100 | 100 |
| 44 | 5-(2-naphthyl)-1H-tetrazole Relative Dosage (Saturated Solution) | | | |
| | 1.5 | 121 | 109 | 99 |
| | 0 | 100 | 100 | 100 |

TABLE 4-continued

Results of platelet function testing, including all the active compounds

| Compound No. | | % clump time increase | % stick time increase | % clot time increase |
|---|---|---|---|---|
| 36 | thiazol-2-amine Relative Dosage (Saturated Solution) | | | |
| | 3.2 | 115 | 116 | 108 |
| | 2.4 | 121 | 118 | 104 |
| | 1.6 | 104 | 115 | 101 |
| | 0 | 100 | 100 | 100 |
| 45 | 5-(2-chloroethyl)-4-methyl-thiazole Dosage (mg/ml) | | | |
| | 6.7 | 119 | 108 | 101 |
| | 0 | 100 | 100 | 100 |
| 73 | 4-(2H-tetrazol-5-yl)benzonitrile Relative Dosage (Saturated Solution) | | | |
| | 1.4 | 118 | 111 | 99 |
| | 0 | 100 | 100 | 100 |
| 13 | 4-(1H-tetrazol-5-yl)benzaldehyde Relative Dosage (Saturated Solution) | | | |
| | 4.3 | 117 | 104 | 243 |
| | 3.2 | 103 | 102 | 194 |
| | 2.1 | 100 | 92 | 151 |
| | 0.4 | 100 | 96 | 96 |
| | 0 | 100 | 100 | 100 |
| 33 | 4-methyl-1,2,4-triazole-3-thiol Dosage (mg/ml) | | | |
| | 6.7 | 115 | 123 | 108 |
| | 5 | 100 | 119 | 100 |
| | 0 | 100 | 100 | 100 |
| 75 | 4-methylthiazole Dosage (mg/ml) | | | |
| | 10.7 | 164 | 155 | 122 |
| | 5.3 | 136 | 132 | 114 |
| | 2.7 | 126 | 123 | 108 |
| | 1.3 | 109 | 102 | 106 |
| | 0.7 | 115 | 106 | 103 |
| | 0 | 100 | 100 | 100 |
| 84 | 1H-imidazole-2-thiol Dosage (mg/ml) | | | |
| | 23.3 | 149 | 142 | 128 |
| | 11.7 | 121 | 111 | 110 |
| | 6.7 | 113 | 105 | 99 |
| | 0 | 100 | 100 | 100 |
| 77 | 1H-indol-3-ylmethanol Dosage (mg/ml) | | | |
| | 23.3 | 140 | 100 | 126 |
| | 11.7 | 116 | 114 | 108 |
| | 6.7 | 109 | 97 | 105 |
| | 3.3 | 81 | 86 | 104 |
| | 0.7 | 95 | 92 | 102 |
| | 0 | 100 | 100 | 100 |
| 88 | (5S)-5-hydroxy-1-(4-hydroxy-3-methoxy-phenyl)decan-3-one Dosage (mg/ml) | | | |
| | 23.3 | 128 | 132 | 100 |
| | 11.7 | 111 | 110 | 104 |
| | 6.7 | 106 | 101 | 102 |
| | 3.3 | 107 | 100 | 104 |
| | 0 | 100 | 100 | 100 |
| 90 | 5-[(3R or 3S)-dithiolan-3-yl]pentanoic acid Dosage (mg/ml) | | | |
| | 23.3 | 129 | 136 | 110 |
| | 11.7 | 110 | 110 | 100 |
| | 6.7 | 97 | 100 | 104 |
| | 3.3 | 102 | 104 | 97 |
| | 0 | 100 | 100 | 100 |

TABLE 4-continued

Results of platelet function testing, including all the active compounds

| Compound No. | | % clump time increase | % stick time increase | % clot time increase |
|---|---|---|---|---|
| 15 | 1-[4-(1H-tetrazol-5-yl)phenyl]ethanone Relative Dosage (Saturated Solution) | | | |
| | 0 | 100 | 100 | 100 |
| | 4.3 | 100 | 98 | 253 |
| | 3.3 | 93 | 94 | 179 |
| | 2.2 | 78 | 84 | 148 |
| | 0.4 | 93 | 90 | 97 |
| 2 | 5-phenyl-1H-triazole | | | |
| | 0.000 | 100 | 100 | 100 |
| | 0.67 | 109 | 103 | 104 |
| 93 | tetrazole | | | |
| | 0.000 | 100 | 100 | 100 |
| | 2.3 | 211 | 193 | 150 |
| | 2.000 | 194 | 173 | 128 |
| | 1.000 | 116 | 116 | 114 |
| 94 | 5-methylthiazole | | | |
| | 7 | 188 | 170 | 117 |
| | 2 | 119 | 109 | 102 |
| | 0 | 100 | 100 | 100 |
| 99 | 1H-triazole | | | |
| | 7 | 103 | 99 | 108 |
| | 2 | 99 | 104 | 103 |
| | 0 | 100 | 100 | 100 |
| 102 | carbamimidoylthiourea | | | |
| | 2.3 | 100 | 96 | 103 |
| | 2 | 101 | 106 | 101 |
| | 1 | 98 | 101 | 108 |
| | 0 | 100 | 100 | 100 |

Example 3

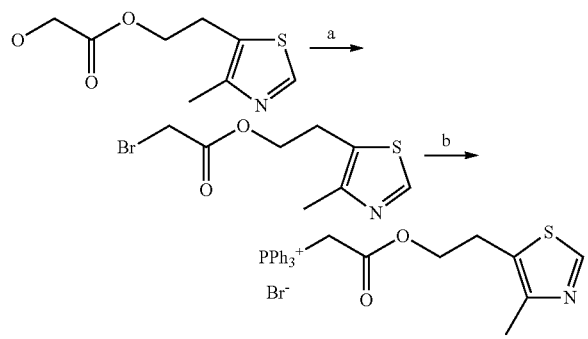

a. Preparation of 2-(4-methylthiazol-5-yl)ethyl 2-bromoacetate

Under an atmosphere of $N_2$, 2-(4-methylthiazol-5-yl)ethanol (970 mg) was dissolved in dry chloroform (4 ml). 2-bromoacetyl bromide (1.4 g) was added dropwise over the course of 30 minutes at 0° C. The reaction mixture was then stirred at room temperature for 2 before saturated $NaHCO_3$ (20 ml) was added. The mixture was then extracted with chloroform (3×20 ml), the combined organic layers were dried with anhydrous $MgSO_4$, and the solvent was removed under reduced pressure. The crude product was purified using column chromatography using chloroform as the eluent to give the final product (850 mg, 48% yield). $^1$H NMR (400 MHz, CDCl$_3$) δ 8.56 (s, 1H), 4.29 (t, 2H, $^3$J=6.5 Hz), 3.80 (s, 2H), 3.10 (t, 2H, $^3$J=6.5 Hz), 2.38 (s, 3H).

b. Preparation of (2-(2-(4-methylthiazol-5-yl)ethoxy)-2-oxoethyl)triphenylphosphonium bromide (49)

Under an atmosphere of $N_2$, 2-(4-methylthiazol-5-yl)ethyl 2-bromoacetate (176 mg) and triphenylphosphine (175 mg) were dissolved in toluene (1.5 ml). The reaction mixture was stirred for 48 hours at room temperature. The resulting white precipitate was filtered, triturated with toluene, and purified by recrystallization from ethanol to give the final product (110 mg, 31% yield). $^1$H NMR (400 MHz, D$_2$O) δ 8.63 (s, 1H), 7.60-7.85 (m, 15H), 5.65 (d, 2H, $^3$J=13.6 Hz), 4.22 (t, 2H, $^3$J=5.7 Hz), 2.93 (t, 2H, $^3$J=5.7 Hz), 2.13 (s, 3H).

Example 4

Preparation of methyl 2-(1H-tetrazol-5-yl)acetate (11)

2-(1H-tetrazol-5-yl)acetic acid (compound 82) (15 mg) was dissolved in methanol (2 ml) containing concentrated sulfuric acid (200 μL). The mixture was refluxed for 6 hours, cooled to room temperature, and then diluted with water (10 ml). The solution was then extracted with ethyl acetate (5×10 ml), and the combined organic layers were dried with anhydrous $MgSO_4$. The solvent was subsequently removed under reduced pressure to give the final product (9 mg, 54% yield). $^1$H NMR (400 MHz, CDCl$_3$) δ 4.19 (s, 2H), 3.87 (s, 3H).

Example 5

Preparation of D-ergothioneine (51)

D-ergothioneine was synthesized starting from commercially available D-histidine (Sigma-Aldrich). D-histidine methyl ester dihydrochloride was synthesized according to a modified literature procedure in which D-histidine was substituted for L-histidine.[1] Using D-histidine methyl ester dihydrochloride instead of the L-enantiomer, D-ergothioneine was synthesized following the method of Yadan and Xu.[2]

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

What is claimed is:

1. A method of reducing platelet activation in a human subject having an inappropriately high level of platelet activation, comprising a step of administering to the subject a pharmaceutical formulation comprising an effective amount of a tetrazole or triazole compound selected from the group consisting of: 1H-tetrazol-5-amine, 4,5-dibromo-1H-1,2,3 triazole, 5-(2H-tetrazol-5-ylmethyl)-2H-tetrazole, 2H-tetrazole-5-carboxamide, 5-(2H-tetrazol-5-yl)-2H-tetrazole, ethyl 2-(1H-tetrazol-5-yl)acetate, and 5-methylsulfanyl-1H-tetrazole, or a pharmaceutically acceptable salt thereof, whereby platelet activation in the subject is reduced.

2. The method of claim 1, further comprising a step of determining an inappropriately high level of platelet activation by an in vitro assay of the subject's platelet function, said assay comprising at least one of clumping, clotting, and sticking.

3. The method of claim 1, wherein the compound is selected from the group consisting of: 1H-tetrazol-5-amine, 4,5-dibromo-1H-1,2,3 triazole, and 5-methylsulfanyl-1H-tetrazole.

4. The method of claim 3, further comprising a step of determining an inappropriately high level of platelet activation by an in vitro assay of the subject's platelet function, said assay comprising at least one of clumping, clotting, and sticking.

5. The method of claim 1, wherein the compound is selected from the group consisting of: 1H-tetrazol-5-amine, 5-(2H-tetrazol-5-ylmethyl)-2H-tetrazole, 2H-tetrazole-5-carboxamide, 5-(2H-tetrazol-5-yl)-2H-tetrazole, ethyl 2-(1H-tetrazol-5-yl)acetate, and 5-methylsulfanyl-1H-tetrazole.

6. The method of claim 5, further comprising a step of determining an inappropriately high level of platelet activation by an in vitro assay of the subject's platelet function, said assay comprising at least one of clumping, clotting, and sticking.

* * * * *